US009074238B2

(12) United States Patent
Hu et al.

(10) Patent No.: US 9,074,238 B2
(45) Date of Patent: Jul. 7, 2015

(54) METHODS FOR ENHANCING NEPRILYSIN ACTIVITY AND DEGRADING AMYLOID-BETA PEPTIDES AND OLIGOMERS IN A SUBJECT WITH ALZHEIMER'S DISEASE

(75) Inventors: Chaur-Jong Hu, Taipei (TW); Po-Ting Chen, Taipei (TW); Rita P.-Y. Chen, Taipei (TW); Steven Sheng-Shih Wang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 13/467,036

(22) Filed: May 8, 2012

(65) Prior Publication Data

US 2013/0102498 A1 Apr. 25, 2013

Related U.S. Application Data

(60) Provisional application No. 61/483,680, filed on May 8, 2011.

(51) Int. Cl.

| | |
|---|---|
| ***A61K 31/235*** | (2006.01) |
| ***C12Q 1/37*** | (2006.01) |
| ***C07C 49/248*** | (2006.01) |
| ***C07C 59/84*** | (2006.01) |
| ***C07C 59/90*** | (2006.01) |
| ***C07K 7/06*** | (2006.01) |
| ***C07C 49/255*** | (2006.01) |
| ***C07C 49/235*** | (2006.01) |
| ***C07C 225/22*** | (2006.01) |
| ***C12Q 1/02*** | (2006.01) |
| ***G01N 33/50*** | (2006.01) |
| ***C07C 49/223*** | (2006.01) |
| ***C07K 14/47*** | (2006.01) |

(52) U.S. Cl.

CPC ... *C12Q 1/37* (2013.01); *C07K 7/06* (2013.01); *C07C 49/255* (2013.01); *C07C 59/90* (2013.01); *C07C 49/248* (2013.01); *C07C 49/235* (2013.01); *C07C 225/22* (2013.01); *C12Q 1/025* (2013.01); *A61K 31/235* (2013.01); *G01N 33/5058* (2013.01); *G01N 2333/4709* (2013.01); *G01N 2500/00* (2013.01); *G01N 2800/2821* (2013.01); *C07C 49/223* (2013.01); *C07K 14/4711* (2013.01)

(58) Field of Classification Search

None

See application file for complete search history.

(56) References Cited

U.S. PATENT DOCUMENTS

| | | | |
|---|---|---|---|
| 6,887,898 | B1 | 5/2005 | Kim |
| 7,279,501 | B2 | 10/2007 | Kim |
| 7,282,523 | B2 | 10/2007 | Kim |
| 7,728,043 | B2 | 6/2010 | Kim |
| 2006/0008842 | A1 | 1/2006 | Takaomi et al. |

OTHER PUBLICATIONS

Venkateswarlu et al., "Synthesis and biological evaluation of polyhydroxycurcuminoids," Bioorg. Med. Chem. 2005, 13:6374-6380.*

Ayoub et al., "Influence of Selected Natural Products on Neutral Endopeptidase Activity and β-Amyloid Production in SK-N-SH Cells," Pharm. Biol. 2008, 46:425-432.*

Eckman EA, et al. Regulation of steady-state beta-amyloid levels in the brain by neprilysin and endothelin-converting enzyme but not angiotensin-converting enzyme. J Biol Chem. Oct. 13, 2006;281(41):30471-8. Epub Aug. 14, 2006.

Farris, W., Partial loss-of-function mutations in insulin-degrading enzyme that induce diabetes also impair degradation of amyloid beta-protein. Am J Pathol. Apr. 2004;164(4):1425-34.

S.S. El-Amouri, et al., Neprilysin: an enzyme candidate to slow the progression of Alzheimer's disease. Am. J. Pathol. 172 (2008) 1342-1354.

Yinxing Liu, et al., In vitro and in vivo degradation of Aβ peptide by peptidases coupled to erythrocytes. Peptides. Dec. 2007 ; 28(12): 2348-2355.

Kurochkin, IV, et al. (1994). Alzheimer's beta-amyloid peptide specifically interacts with and is degraded by insulin degrading enzyme. FEBS Lett. 345 (1): 33-37.

Qiu, WQ, et al., (1998). "Insulin-degrading Enzyme Regulates Extracellular Levels of Amyloid β-Protein by Degradation". The Journal of Biological Chemistry 273 (49): 32730-8.

* cited by examiner

*Primary Examiner* — Samuel Woolwine
*Assistant Examiner* — Kaijiang Zhang
(74) *Attorney, Agent, or Firm* — Hsiu-Ming Saunders; Intellectual Property Connections, Inc.

(57) ABSTRACT

A method of enhancing neprilysin activity and/or degrading amyloid-β peptides and/or oligomers in a subject with Alzheimer's disease is disclosed. The method comprises administering to the subject a compound selected from the group consisting of

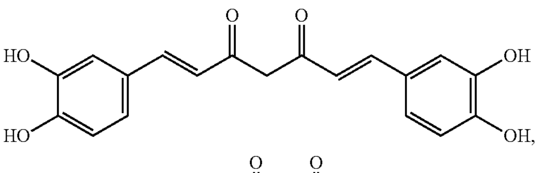

and

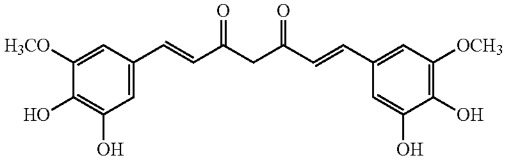

in a therapeutically effective amount to enhance the neprilysin activity and/or degrade the amyloid-β peptides and oligomers in the subject. Methods of improving symptoms and/or retarding progression of Alzheimer's disease and prophylactic treatment and/or treatment of Alzheimer's disease are also disclosed.

3 Claims, 13 Drawing Sheets

(A)

(B)

| COMPOUND | | | |
|---|---|---|---|
| No. | FORMULA | No. | FORMULA |
| 1 |  | 14 |  |
| 2 |  | 15 |  |
| 3 |  | 16 |  |
| 4 |  | 17 |  |
| 5 |  | 18 |  |
| 6 |  | 19 |  |
| 7 |  | 20 |  |
| 8 |  | 21 |  |
| 9 |  | 22 |  |
| 10 |  | 23 |  |
| 11 |  | 24 |  |
| 12 |  | 25 |  |
| 13 |  | 26 |  |

METHODS FOR ENHANCING NEPRILYSIN ACTIVITY AND DEGRADING AMYLOID-BETA PEPTIDES AND OLIGOMERS IN A SUBJECT WITH ALZHEIMER'S DISEASE

CROSS-REFERENCE TO RELATED APPLICATIONS

This application claims the priority of U.S. Provisional Patent Application Ser. No. 61/483,680 filed May 8, 2011 titled "COMPOSITIONS AND METHODS FOR DETECTING AMYLOID-β-DEGRADING ENZYME ACTIVITY," which is incorporated herein by reference in its entirety.

TECHNICAL FIELD OF THE INVENTION

This invention relates generally to the field of screening for agents that are useful for treatment of diseases, such as Alzheimer's disease, that are related to amyloid-β degradation activity. In particular, the invention relates to use of a quenched fluorogenic peptide substrate for assaying the activity of amyloid β degrading enzymes that are known to be involved in Alzheimer's disease. More specifically, the invention provides a specific substrate for the assay of neprilysin and insulin degrading enzyme activities.

BACKGROUND OF THE INVENTION

About 100,000 people die of AD every year and, with the increasing human lifespan, more and more people will suffer from this malady. AD patients suffer from slow loss of function over a period that can be as long as twenty years, and care costs for AD patients are therefore enormous, making research into therapeutic strategies for AD pressing and valuable. During the last two decades, scientists have expended much effort on understanding this disease, but no effective treatment has yet been found. Prevention of Aβ production, blockage of Aβ accumulation in plaques, reducing level of soluble Aβ in the brain, and disaggregation of existing amyloid plaques have being envisaged as potential approaches to attenuating the progression of AD [9; 31]. Of these, methods aimed at the proteolytic mechanisms associated with the biogenesis and degradation of Aβ are promising avenues for intervention [11; 14; 16; 18].

Alzheimer's disease (AD) is a progressive neurodegenerative disease and is the most prevalent form of age-related dementia [1]. Upon post-mortem examination or autopsy of brain tissue, the two primary pathological features observed in AD are the formation of extracellular senile plaques and intraneuronal neurofibrillary tangles [2; 3; 4]. The key constituent of senile plaques has been identified as a 39-43 amino acid polypeptide, β-amyloid (Aβ), generated by the sequential proteolytic cleavage of a much larger amyloid precursor protein (APP) by β- and γ-secretases [5]. It is widely, but not universally, believed that the accumulation of Aβ as fibrils during AD is a causative event in the neurodegeneration observed in AD and that the Aβ peptide may serve as a significant contributing factor to the onset or progression of AD [6; 7; 8].

To combat AD, considerable effort has been directed towards developing a variety of therapeutic strategies [9; 10; 11]. One branch of this research is focused on preventing the formation of Aβ by the development of β- and γ-secretase inhibitors or on strategies for directly antagonizing Aβ accumulation, using either "plaque-buster" drugs or immunotherapy to aid in clearing the brain of plaques [5; 12]. Given that the abnormal accumulation of Aβ in the brain can be attributed to increased production or decreased degradation of Aβ, the activation of specific proteases that metabolize Aβ, thereby clearing it from the brain, may be a potential treatment for AD [13; 14; 15; 16; 17].

U.S. Pat. No. 6,887,898 (2005) discloses the treatment of β-amyloid protein induced cytotoxicity based on the antioxidant activity of a compound with a curcumin-like scaffold. U.S. Pat. No. 7,282,523 (2007) and U.S. Pat. No. 7,279,501 (2007) disclose natural product compounds isolated from turmeric, gingko biloba, and ginger, and synthetic chemical analogues thereof, that protect cells from Aβ-induced toxicity. U.S. Pat. No. 7,728,043 (2010) discloses similar natural compounds useful for treating beta-amyloid protein-involved ocular disease including age-related macular degeneration and glaucoma.

Proteases that degrade the amyloid beta-protein (Aβ) are important regulators of brain Aβ levels in health and in Alzheimer's disease. It has been suggested that amyloid-degrading enzymes might be good therapeutic targets in Alzheimer's disease [14; 16] and Neprilysin (NEP) has been singled out as the ideal candidate [15; 17; 18]. Neprilysin (NEP, EC 3.4.24.11), also known as neutral endopeptidase, enkephalinase, CD10, and common acute lymphoblastic leukemia antigen, is a type II zinc-containing transmembrane metalloproteinase. [18] It is found in the mammalian central nervous system and a wide range of peripheral tissues, including the kidney and lung [19; 20]. Structurally, it consists of a 23-residue N-terminal intracellular domain, a 24-residue membrane-spanning domain, and a 699-residue extracellular catalytic domain, allowing NEP to act as an ectoenzyme catalyzing peptide hydrolysis in the extracellular milieu [21]. Evidence suggests that NEP is inactivated or downregulated during both the early stage of AD and aging [22; 23]. An inverse correlation is seen between NEP levels and either Aβ levels or extent of amyloid plaque formation [18; 24]. Moreover, NEP is capable of degrading soluble oligomeric Aβ as well as monomeric Aβ [25]. A two-fold increase in Aβ40 and Aβ42 levels was found in NEP knock-out mice compared to knock-out mice for other Aβ-degrading enzymes [26]. Furthermore, NEP is mainly found in presynaptic terminals, where Aβ accumulation takes place [27]. NEP is therefore regarded as a potential therapeutic target and its enhanced expression might represent a promising approach to the treatment of AD [28].

US Pat. Pub. App. No. 20060008842 (Ser. No. 10/512,588) describes a method for measuring measure neprilysin activity in nerve cells using the substrate glutaryl-alanyl-alanyl-phenylalanyl-4-methoxy-2-naphthylamide. When this substrate is degraded by neprilysin and aminopeptidase, the degraded product, 4-methoxy-2-naphthylamine, interacts with nitrosalicylaldehyde to form an insoluble yellow fluorescent substance. No enzyme selectivity is mentioned. The visualtion method is complicated and slower.

Neprilysin (NEP) has been singled out as the most promising candidate for use in the degradation of Aβ as a therapy for Alzheimer's disease.

Neprilysin is also associated with other biochemical processes, and is particularly highly expressed in kidney and lung tissues. Inhibitors have been designed with the aim of developing analgesic and antihypertensive agents that act by preventing neprilysin's activity against signaling peptides such as enkephalins, substance P, endothelin, and atrial natriuretic factor. [39]

Associations have been observed between neprilysin expression and various types of cancer; however, the relationship between neprilysin expression and carcinogenesis remains obscure. In cancer biomarker studies, the neprilysin gene is often referred to as CD10 or CALLA. In some types of cancer, such as metastatic carcinoma and some advanced melanomas, neprilysin is overexpressed; [38] in other types, most notably lung cancers, neprilysin is downregulated.

Known alternatively as insulysin or insulin protease, Insulin Degrading Enzyme (IDE) is a large zinc-binding protease of the M16A metalloprotease subfamily known to cleave multiple short polypeptides that vary considerably in sequence. IDE was first identified by its ability to degrade the B chain of the hormone insulin. Considerable interest in IDE has been stimulated due to the discovery that IDE can degrade amyloid beta (Aβ), a peptide implicated in the pathogenesis of Alzheimer's disease. [40] The primary neuropathology observed is the formation of amyloid plaques and neurofibrillary tangles. Other findings have suggested that IDE activity is capable of joining of several Aβ fragments together to form oligomers. [41]

Therefore, what is needed is a rapid and efficient visulation method for detecting the activity of neprilysin and IDE using a substrate that is selective for neprilysin.

SUMMARY OF THE INVENTION

The invention provides novel substrates for the selective and efficient detection of amyloid-beta (Aβ) degrading enzyme activity, such as, Neprilysin (NEP) and insulin degrading enzyme (IDE), associated with Alzheimer's disease.

The invention provides a quenched fluorogenic peptide substrate containing the first seven residues of the Aβ peptide plus a C-terminal Cys residue was synthesized to detect neprilysin activity, and a fluorophore attached to the C-terminal Cys whose fluorescence is quenched by a quencher linked to the N-terminus of the peptide. When this peptide substrate was degraded by an amyloid-beta degrading endopeptidase, fluorescence is produced. The assay comprises a sensitive detection system for endopeptidase activity.

The invention provides an assay system that is extremely sensitive to NEP and insulin degrading enzyme, but insensitive, or much less sensitive, to other Aβ-degrading enzymes. The invention provides a cell-based assay system for high-throughput screening of compounds able to enhance NEP activity in cells.

The invention further provides a number of compounds—curcumin and curcumin analogs—that were identified by the assays of the claimed invention and demonstrated an ability to enhance or inhibit NEP activity in a human cell.

Because neprilysin is a membrane protein, the inventors of the present invention used a quenched fluorogenic peptide as a substrate for neprilysin on membrane. This peptide is soluble. This peptide has a fluorophore and a quencher attached at its two ends. The fluorescence is quenched due to the existence of the quencher. When it is cleaved by neprilysin, the fluorescence is no longer be quenched. The fluorescence increases.

The invention provides an assay wherein a compound to be screened for NEP activity is added to medium containing human SH-SY5Y cells, and then the quenched fluorogenic peptide is added. The higher the level of neprilysin in the cells, the higher the fluorescence in the medium. The fluorescence assat can be performed on a 96-well microplate. Only 200 μl culture medium is enough for detection. One milligram of the synthetic peptide substrate can be used to screen more than six thousand compounds. The assay is ideal for high throughput screening compounds which can enhance neprilysin production or activity in a cell.

The invention provides a quenched fluorogenic peptide substrate containing the first seven residues of the Aβ peptide plus a C-terminal Cys residue synthesized to detect neprilysin activity. A fluorophore is attached to the C-terminal Cys and its fluorescence is quenched by a quencher linked to the N-terminus of the peptide. When this peptide substrate is degraded by an endopeptidase, fluorescence is produced and proved to be a sensitive detection system for endopeptidase activity.

The invention provides an assay system that is extremely sensitive to NEP and insulin degrading enzyme (IDE), but insensitive, or much less sensitive, to other Aβ-degrading enzymes. The assay system is sensitive enough to detect as low as 0.10 nM NEP. Only 0.46 μM peptide substrate is sufficient for detecting 1 nM NEP, and only 2 μM peptide substrate is sufficient for detecting 0.1 nM NEP as compared to other known commercial substrates which require 40 μM peptide for detecting 2 nM NEP.

The invention provides a cell-based assay system developed for the high-throughput screening of chemicals that are able to enhance NEP production in human SH-SY5Y cells.

The invention relates to a peptide substrate for detection of amyloid-β degrading enzyme activity, the substrate comprising: (a) a peptide comprising a cleavage site for an amyloid-β degrading enzyme; and (b) a fluorophor coupled to the N-terminal end of the peptide and a quencher coupled with the C-terminal end of the peptide, or a quencher coupled to the N-terminal end of the peptide and a fluorophor coupled with the C-terminal end of the peptide.

In some embodiments, the amyloid-β degrading enzyme is selected from the group consisting of a neprilysin (NEP) or an insulin degrading enzyme (IDE).

In some embodiments, the fluorophore is selected from the group consisting of fluorescein, fluorescein derivatives, rhodamines, tetramethylrhodamines, coumarins, resorufins, pyrenes, anthracenes, phenylenes, phthalocyanines, cyanines, xanthenes, amidopyrylium dyes, oxazines, quadrain dyes, carbopyronines, NBD derivatives, BODIPY fluorophores, ALEXA fluorophores, ALEXA-350, lanthanide chelates, metalloporphyrins, NIR fluorophores, rhodol dyes, naphthalimides and porphyrins.

In some embodiments, the quencher is a non-fluorescent chromophore selected from the group consisting of DABCYL, DABMI, Malachite Green and Coumarin.

In some embodiments, the peptide comprises at least 7 consecutive N-terminal amino acids of the amyloid-β peptide.

In some embodiments, the peptide comprises residues 1-7 of the amyloid-β peptide and a cysteine residue at the C-terminal end with the sequence DAEFRHDC.

In some embodiments, the peptide is sensitive to cleavage by the Aβ degrading enzymes neprisyn (NEP) and insulin degrading enzyme (IDE), but has low or no sensitivity to cleavage by the Aβ degrading enzymes endothelin-converting enzymes 1 (ECE-1), angiotensin-converting enzyme (ACE), matrix metalloproteinases (MMPs) MMP-3 and MMP-9, and plasmin.

The present invention relates to a method for detection of amyloid β (Aβ) degrading enzyme activity, the method comprising: providing a cell-free or cell-based assay system suspected of comprising a Aβ degrading enzyme; contacting the assay system with a quenched fluorogenic peptide substrate according to the invention; and measuring a level of fluorescence in the system, wherein the level of fluorescence is indicative of the activity of an Aβ degrading enzyme.

In some embodiments the method of detection further comprises diagnosing Alzheimer's disease (AD), aiding in diagnosis of AD, monitoring AD in AD patients, tracking disease progression in AD patients, stratifying AD patients for mild, moderate or severe AD, and prediagnosing a likelihood of progression to AD of patients with mild cognitive impairment (MCI).

The present invention relates to a method for screening compounds suspected of having an agonist or antagonist effect on amyloid β (Aβ) degrading enzyme activity, the method comprising: providing a cell-free or cell-based assay system comprising an Aβ degrading enzyme and a quenched fluorogenic peptide substrate according to the invention; contacting the assay system with a test compound; and measuring a change in the level of fluorescence in the system prior to and after contacting the system with the test compound, wherein an increase or decrease in the level of fluorescence is indicative of the agonist or antagonist activity of the test compound.

In some embodiments the methods of the invention comprise a nerve cell derived system, a cultured nerve cell or human neuroblastoma SH-SY5Y cells.

In some embodiments the methods of the invention comprise an assay sensitive to cleavage by the Aβ degrading enzymes neprilysin (NEP) and insulin degrading enzyme (IDE), but has low or no sensitivity to cleavage by the Aβ degrading enzymes endothelin-converting enzymes 1 (ECE-1), angiotensin-converting enzyme (ACE), matrix metalloproteinases (MMPs) MMP-3 and MMP-9, and plasmin.

The invention relates to a compound, or a pharmaceutical composition comprising the compound for enhancing the activity of neprilysin, wherein the compound is obtainable using the screening method according to the invention. In some embodiments, the pharmaceutical is suitable for use as a preventive and/or therapeutic agent, a symptom-improving agent or a progression-retarding agent for Alzheimer's disease.

In some embodiments the methods of the invention further comprise, contacting the assay system with somatostatin, a protein containing substantially the same amino acid sequence as somatostatin or its partial peptide, or an agonist of somatostatin receptor, for enhancing neprilysin activity.

In some embodiments the methods of the invention further comprise, contacting the assay system with substance P, a protein containing substantially the same amino acid sequence as substance P or its partial peptide, or an agonist of substance P receptor, for enhancing neprilysin activity.

In some embodiments the methods of the invention further comprise, enhancing the activity or expression of neprilysin by promoting the activity of somatostatin receptor in a mammal.

In some embodiments the methods of the invention further comprise, enhancing the activity or expression of neprilysin by contacting the assay system with an antagonist of pituitary adenylate cyclase-activating polypeptide receptor.

In some embodiments the methods of the invention further comprise, enhancing the activity or expression of neprilysin by contacting the assay system with an antagonist of vasoactive intestinal peptide receptor.

In some embodiments the screening method of the invention further comprises high-throughput screening.

In some embodiments the high-throughput screening is carried out in 96- or 384- or 1536-well plates.

In some embodiments the assay system comprises a total volume of about 200, 300, 400, 500 or 1000 μL.

In some embodiments the high-throughput screening comprises screening 100, 200, 300, 400, 500, 1000, 10,000, 20,000, 50,000 or 100,000 test compounds.

The invention relates to compounds identified by the screening or high throughput screening methods of the invention that enhance neprilysin or insulin degrading enzyme activity in a cell, and pharmaceutical compositions comprising such compounds. The pharmaceutical compositions are suitable for use as a preventive and/or therapeutic agent, a symptom-improving agent or a progression-retarding agent for Alzheimer's disease.

Examples of such compounds include, but are not limited to, somatostatin, a protein containing substantially the same amino acid sequence as somatostatin or its partial peptide, or an agonist of somatostatin receptor; substance P, a protein containing substantially the same amino acid sequence as substance P or its partial peptide, or an agonist of substance P receptor; an agent for promoting the activity of somatostatin receptor in a mammal; an antagonist of pituitary adenylate cyclase-activating polypeptide receptor; or an antagonist of vasoactive intestinal peptide receptor.

The present invention and other objects, features, and advantages of the present invention will become further apparent in the following Detailed Description of the Invention and the accompanying Figures and embodiments.

BRIEF DESCRIPTION OF THE FIGURES

(FIG. 6A) Fluorescence increase of different concentrations of qf-Aβ(1-7)C after digestion with 0.92 nM NEP at 37° C. for 1 h. (FIG. 6B) Fluorescence increase of 1.84 μM qf-Aβ(1-7)C after digestion with different concentrations of NEP at 37° C. for 1 h. (FIG. 6C) Western blot of different concentrations of NEP by anti-NEP antibody.

(FIG. 8A) Fluorescence increase of different concentrations of Dansyl-$^{D}$AGF($pNO_2$)G after digestion with 2 nM NEP at 37° C. for 1 h. (FIG. 8B) Peptide degrading activity of NEP, ECE-1, ACE, IDE, plasmin, MMP-9, and MMP-3 measured using 80 μM Dansyl-$^{D}$AGF($pNO_2$)G at pH 7.5 after incubation at 37° C. for 1 hour.

DETAILED DESCRIPTION OF THE INVENTION

Figure 1:
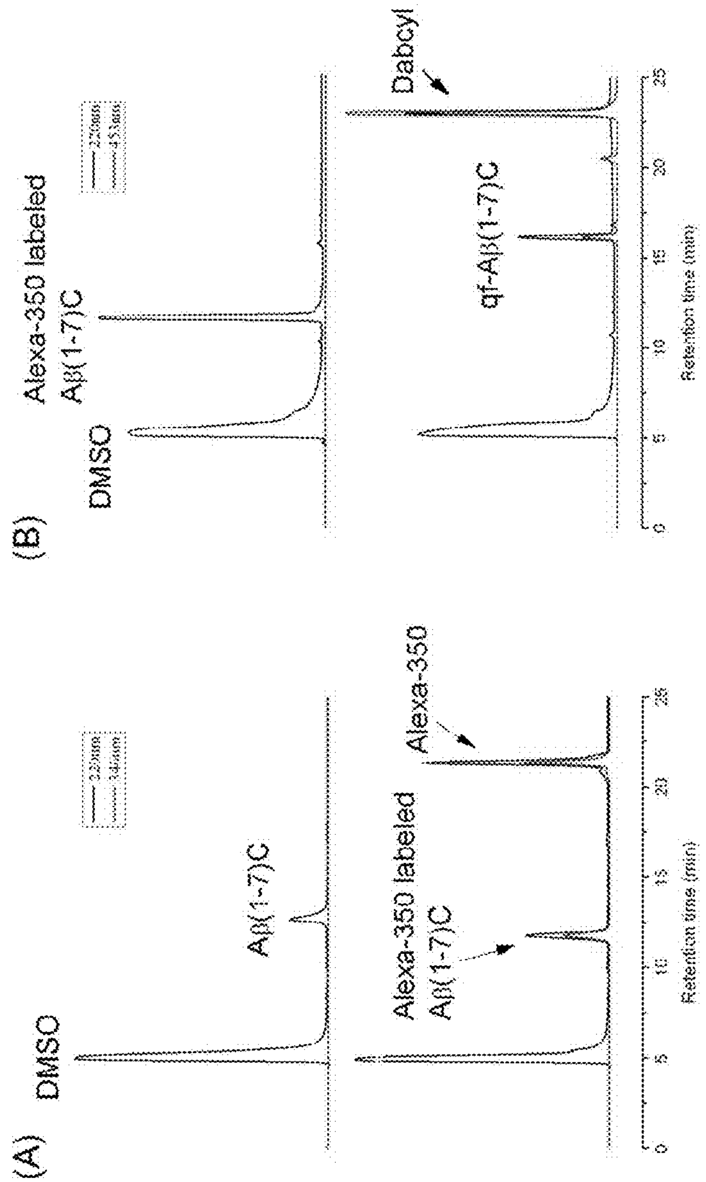
FIG. 1 shows HPLC profiles for the coupling reactions of (A) peptide Aβ(1-7)C with Alexa-350 and (B) the Alexa-350-labeled peptide with Dabcyl. The samples were analyzed by HPLC on a Vydac C18 column and the peptides detected by their absorbance at 220 and 346 (A) or 220 and 453 nm (B). (A) Alexa-350-labeled Aβ(1-7)C was resolved by a 5 min wash with 8% solvent B (0.1% TFA in acetonitrile), 92% solvent A (5% acetonitrile and 0.1% TFA in water), followed by 20 min elution with a linear gradient of 8-22% solvent B. (B) Double-labeled qf-Aβ(1-7)C was resolved using a 30 min linear gradient of 0-100% solvent B.

The production of NEP decreases during the aging process. Due to its Aβ-degrading ability, NEP has been suggested as a potential target in therapeutic strategies for AD. The present invention is directed to a sensitive, cell-based screening system for drugs that increase NEP production. One milligram of the synthetic peptide substrate can be used to screen more than six thousand compounds. Screening of the existing chemical libraries and traditional Chinese medicines is enabled by this system.

Here, the present inventors synthesized a quenched fluorogenic peptide with a high synthetic yield. This peptide was, as expected, an excellent substrate for NEP. The peptide concentration used could be as low as 0.46 μM (only 158 ng of the peptide in 200 μL of buffer is required for each reaction well). The sensitivity of this assay for NEP was very high, with 0.46 nM NEP (7.5 ng in 200 μL buffer) being detected when the concentration of the peptide substrate was increased to 1.84 μM. Compared to previous results, the advantages of this system include: (1) the synthesis of the peptide substrate is much easier [29; 32]; (2) no radiolabel is required [33]; (3) it can sensitively detect NEP and IDE without any pre-treatment or immunocapture step [34; 35]; and (4) it can be used in cell culture to detect NEP levels on the cell membrane.

The high sensitivity of the fluorogenic detection system for IDE is really unexpected. In previous studies [14; 15; 16; 28], cleavage sites for IDE were found in the middle section (sequence 13-28) of the Aβ peptide, but not in the region covered by the peptide (sequence 1-7). The present inventors surmise that dye-labeling of the side-chain of Cys might promote the binding of this peptide to IDE. Unlike NEP, IDE is primarily a cytosolic and peroxisomal enzyme [36]. In the screening system, the reaction was performed on culture medium, so, although the peptide substrate is sensitive to IDE degradation, only the ectoenzyme NEP could cleave the peptide in the culture medium. This cell-based assay system can therefore be used to screen for compounds that promote NEP production.

Synthesis of the Quenched Fluorogenic Protease Substrate

It has been suggested that amyloid-degrading enzymes might be good therapeutic targets in Alzheimer's disease [14; 16] and NEP has been singled out as the best candidate [15; 17; 18]. Since the N-terminal part of the Aβ peptide is water-soluble and contains a NEP cleavage site [14; 15; 16; 28], the present inventors chose the peptide Aβ(1-7)C (amino acid sequence DAEFRHDC; SEQ ID NO: 1), corresponding to residues 1 to 7 of the Aβ peptide followed by an extra cysteine residue at the C-terminus, as the protease substrate.

In one aspect of the invention, suitable derivatives of the Aβ(1-7)C (amino acid sequence DAEFRHDC) may be used, wherein one or more amino acids are replaced by a different amino acid with similar chemical properties or size. For example, D can be replaced by E; A can be replaced by G, S, or T; E can be replaced by D; F can be replaced by Y, or W; R can be replaced by K, or H; and H can be replaced by R, K, N, or Q.

Figure 2:
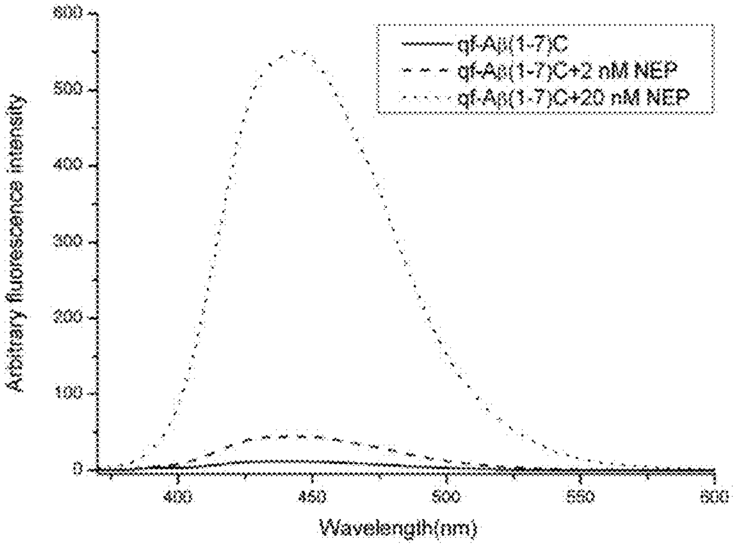
FIG. 2 shows fluorescence emission spectra of qf-Aβ(1-7)C with or without NEP digestion. The excitation wavelength was set at 346 nm.

Chersi et al. [29] reported the synthesis of a double-labeled peptide to assay endopeptidase enzyme activity using a mixed Boc-Fmoc strategy. Here, the present inventors used Fmoc chemistry to synthesize the peptide substrate. The fluorescence reporter Alexa-350 was added to the side-chain of the C-terminal Cys of the peptide. The coupling efficiency was very high and no unlabeled peptide was detected. The labeled peptide was separated from the free dye by HPLC on a Vydac C18 column (FIG. 1A). The quencher, Dabcyl, was then added to the N-terminus of the Alexa-350-labeled peptide and the double-labeled peptide qf-Aβ(1-7)C separated by HPLC. The coupling yield was estimated as ~95% (FIG. 1B). The fluorophore and quencher were separated by 7 amino acids. Alexa-350 fluorescence was quenched by Dabcyl in the double-labeled peptide, but, when the peptide was cleaved by NEP, Dabcyl was no longer close to Alexa-350 to quench the fluorescence and the Alexa-350 fluorescence increased greatly, as shown in FIG. 2.

Fluorogenic Enzyme Assay

Figures 3A, 3B:
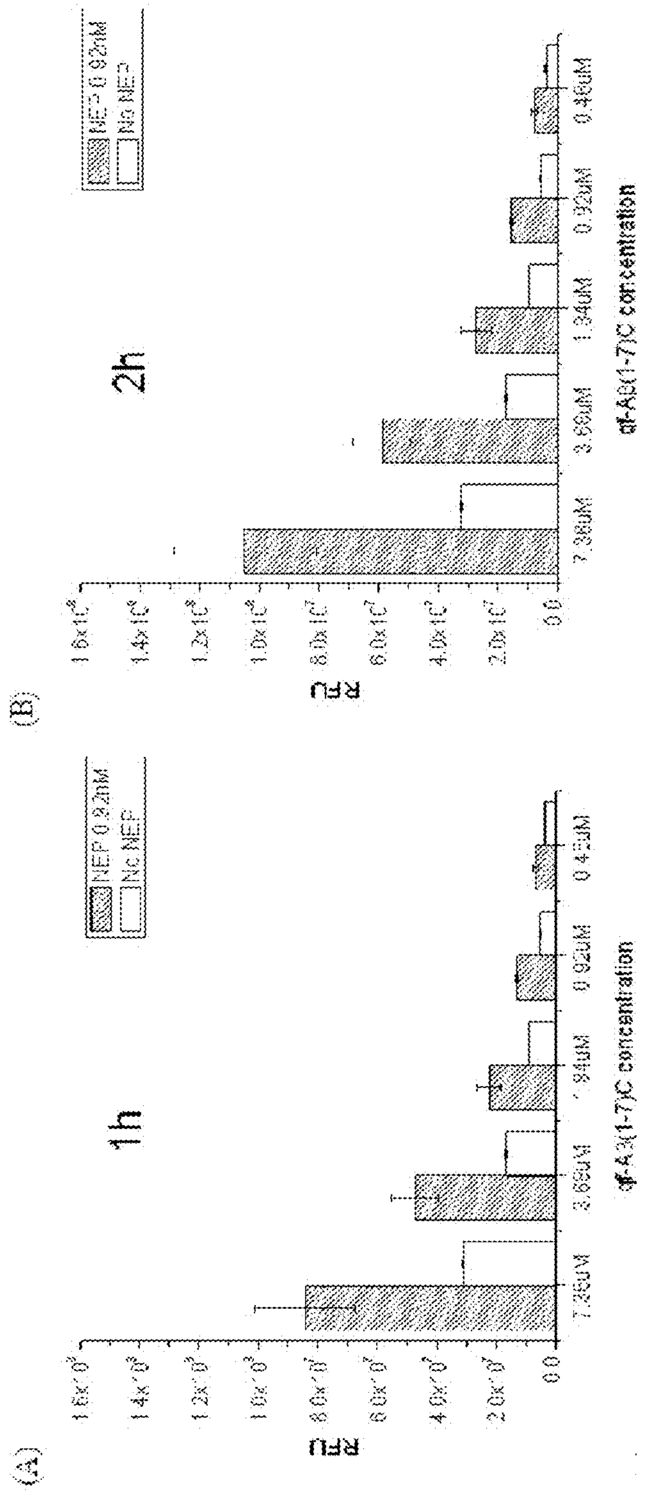
FIG. 3 shows increase in the fluorescence of qf-Aβ(1-7)C after digestion with NEP. Different concentrations of qf-Aβ(1-7)C were incubated with 0.92 nM NEP in 50 mM Tris-HCl (pH 7.5) at 37° C. for 1, 2, 3, or 4 h and the fluorescence was measured at $360_{Ex}/465_{Em}$.
Figures 3C, 3D:
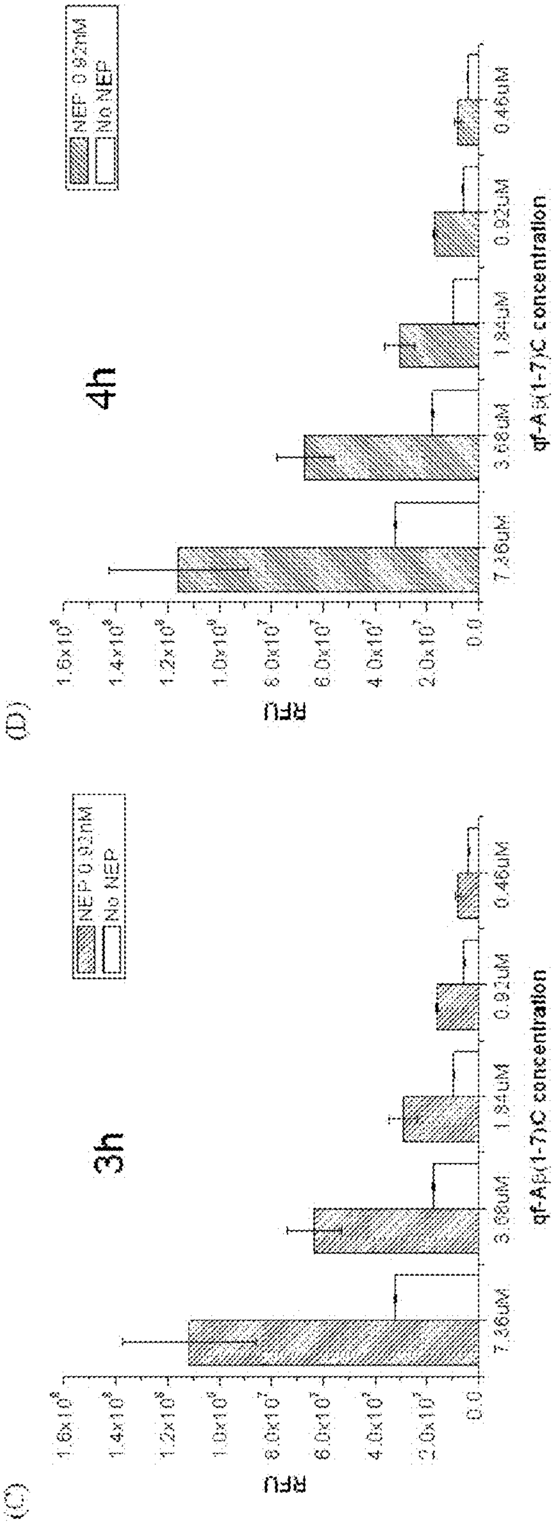
Figures 4A, 4B:
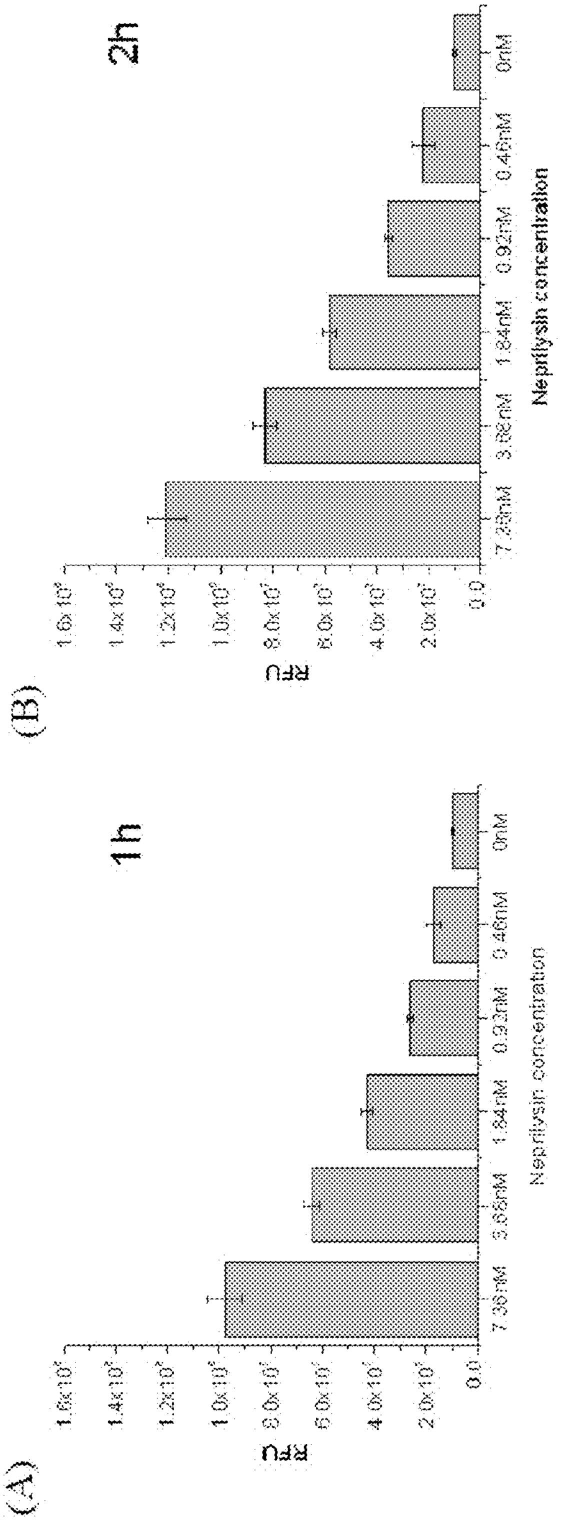
FIG. 4 shows analysis of the sensitivity of NEP detection. 1.84 μM qf-Aβ(1-7)C was mixed with different concentrations of NEP in 50 mM Tris-HCl (pH 7.5) and reacted at 37° C. for 1, 2, 3, or 4 h.
Figures 4C, 4D:
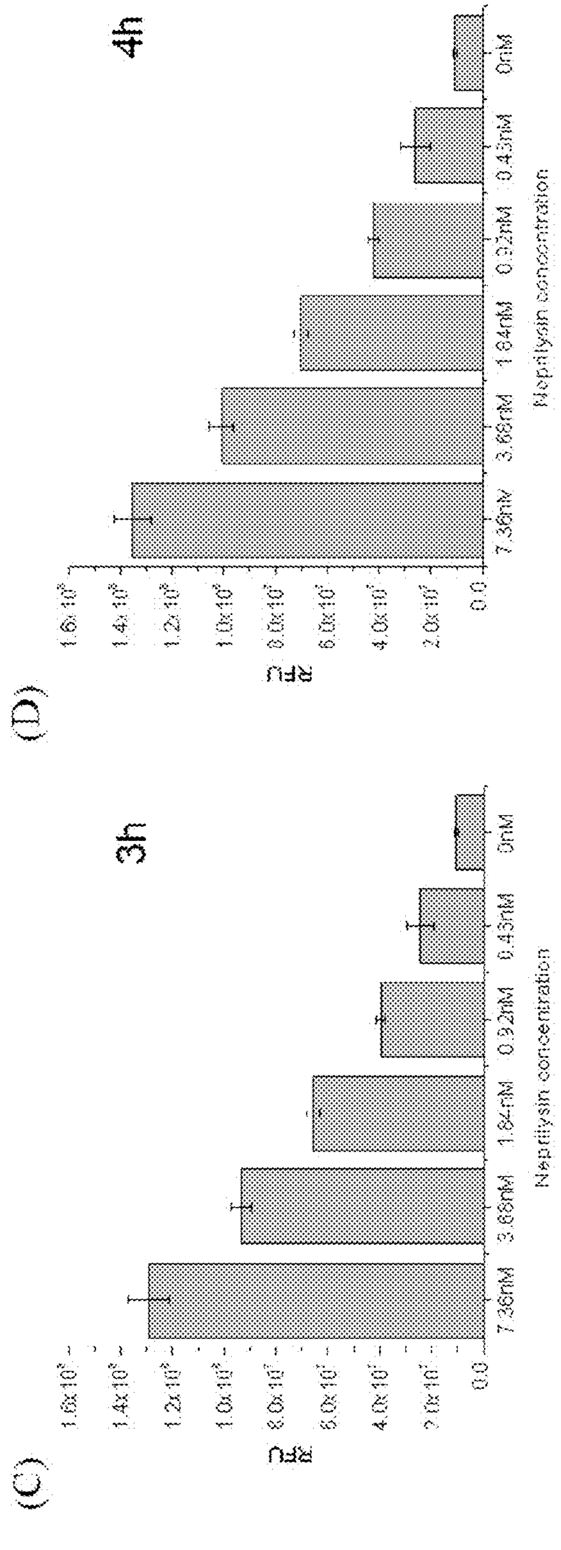

To determine the optimal reaction conditions, 0.92 nM NEP was mixed with different concentrations of qf-Aβ(1-7)C, then, after incubation for 1, 2, 3, or 4 h at 37° C., the peptide-degrading activity of NEP was measured by recording fluorescence emission at 465 nm. The fluorescence intensity increased at least 40-fold with the degradation of the quenched fluorogenic peptide. The results showed that 0.92 nM NEP could be detected when the substrate concentration was as low as 0.46 μM (P<0.00001) (FIG. 3). Although the fluorescence intensity increased with a longer incubation time, the sensitivity of NEP detection did not change significantly. Incubation for 1 h was sufficient for detection. At higher substrate concentrations, the fluorescence intensity was much larger, but the error increased. To test whether the sensitivity of NEP detection was increased when a higher substrate concentration was used, 1.84 μM qf-Aβ(1-7)C was mixed with different concentrations of NEP and reacted at 37° C. for 1, 2, 3, or 4 h and the fluorescence emission at 465 nm measured (FIG. 4). The results showed that increasing the substrate concentration improved the sensitivity of NEP detection, as, when 1.84 μM qf-Aβ(1-7)C was used, NEP was detected at concentrations as low as 0.46 nM (P<0.0001). The substrate concentration of 1.84 μM or more was therefore used in the following studies.

Enzyme Specificity

Figure 5:
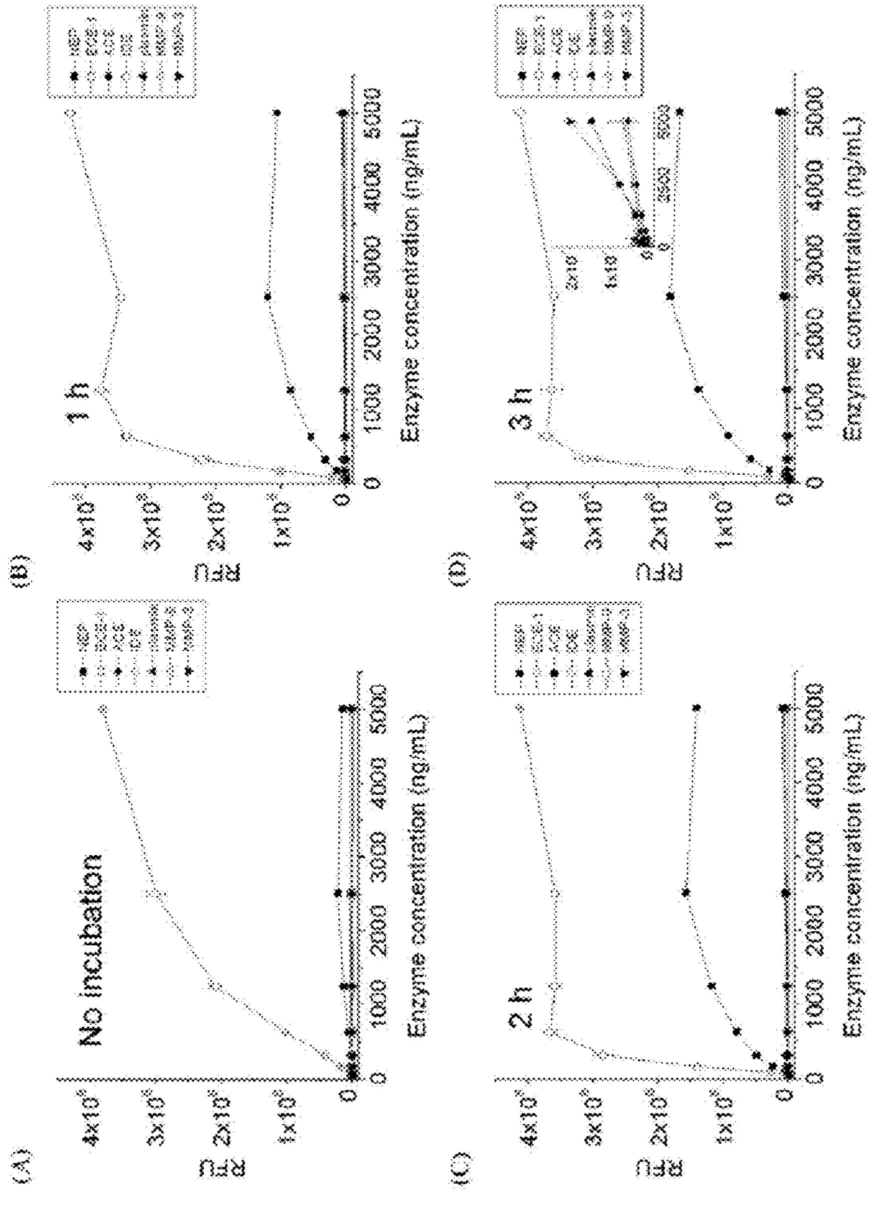
FIG. 5 shows peptide degrading activity of NEP, ECE-1, ACE, IDE, plasmin, MMP-9, and MMP-3 measured using 2 μM qf-Aβ(1-7)C at pH 7.5 before (A) or after incubation for 1 h (B), 2 h (C), or 3 h (D) at 37° C. Inset in (D): expanded on the y-axis.

Recently, the cleavage sites of various Aβ-degrading enzymes, NEP, insulin-degrading enzyme (IDE), endothelin-converting enzymes 1 (ECE-1), angiotensin-converting enzyme (ACE), matrix metalloproteinases (MMPs), and plasmin on the Aβ peptide have been reported [14; 15; 16]. Of these, NEP, ACE, MMP-3, and plasmin were reported to cleave the N-terminal segment (sequence 1-7) of Aβ. The present inventors therefore designed the peptide substrate in this study based on this sequence in order to specifically detect these enzymes. When the present inventors examined the ability of recombinant human NEP, IDE, ACE, ECE-1, MMP-3, MMP-9, and plasmin to cleave the quenched fluorogenic peptide, the results showed that only IDE and NEP were effective (FIG. 5). Surprisingly, the assay was even more sensitive to IDE than to NEP. Within the time needed to make the additions and record the fluorescence, IDE had already greatly degraded the substrate peptide, resulting in a large increase in fluorescence. For the same weight of IDE and NEP, the degradative activity of IDE was higher than that of NEP, despite the fact that no cleavage site for IDE in this peptide has ever been reported. On the other hand, although it has been reported that MMP-3, plasmin, and ACE have a cleavage site within the sequence 1 to 7 of Aβ40 [14], only a very weak fluorescence increase was detected after incubation with MMP-3 and ACE for 3 h in the system (FIG. 5D inset). The system was also much less sensitive to plasmin, ECE-1, or MMP-9.

Sensitivity of the Substrate

The sensitivity of this assay for NEP is very high, with 0.1 nM NEP (1.6 ng in 200 μL buffer) being detected when the concentration of the peptide substrate is increased to 1.84 μM. Compared with other quenched fluorogenic peptide substrates, Mca-RPPGFSAFK(Dnp) does not have enzyme specificity (34); the signal increase of Dansyl-$^{D}$AGF $(pNO_2)$G after digestion is not strong enough, thereby much higher peptide concentration (80 μM) is required; and the synthesis of Abz-GG$^{D}$FLRRV-EDDnp is more complicated (32, 38).

The advantages of this peptide substrate include: (a) the synthesis of the peptide substrate is much easier and the yield is high; (b) this assay only needs very low concentrations of the substrate (e.g.: 0.46 μM), compared with other substrates (tens to hundreds micromolar); and (c) no radiolabel is required.

Detection of Somatostatin-Induced Aβ-Degrading Enzymes

Figure 9:
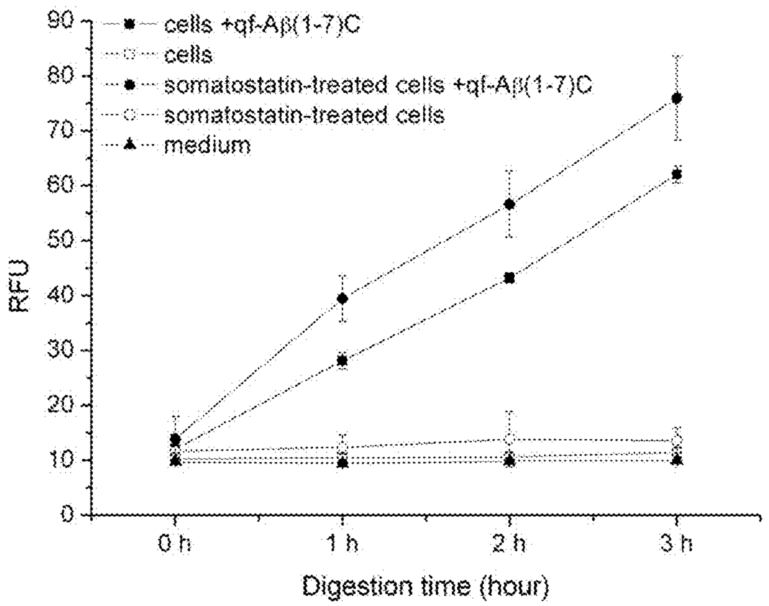
FIG. 9 shows detection of somatostatin-induced Aβ degrading ability on SH-SY5Y cells by the qf-Aβ(1-7)C fluorescence assay system.

In order to develop a high-throughput system for screening compounds that is able to increase NEP production by cells, human SH-SY5Y cells were used. Somatostatin is known to induce NEP production [30]. Since NEP is a cell surface membrane-bound glycoprotein, the assay was performed in cell culture. After treating SH-SY5Y cells with 1 μM somatostatin for 1 day, qf-Aβ(1-7)C was added to the culture at a final concentration of 2 μM and incubation continued. One hundred microliter of medium was withdrawn at 0, 1, 2 or 3 h for fluorescence measurements. As shown in FIG. 9, medium in the absence of peptide ("medium") or medium taken from cell cultures in the absence of peptide with ("somatostatin-treated cells") or without ("cells") somatostatin induction showed little fluorescence. In the absence of added somatostatin, but in the presence of peptide, there was a basal level of NEP production on the cell surface ("cells+qf-Aβ(1-7)C"). After induction by somatostatin for one day, the fluorescence intensity after 1 h of digestion was ~58% higher than in the absence of somatostatin induction ("somatostatin-treated cells+qf-Aβ(1-7)C"), corresponding to an increase in NEP production after somatostatin induction. (FIG. 9). The results therefore show that this assay system can be used to screen drugs that can increase NEP production in cells.

In one embodiment of the present invention, a method of measuring the activity of neprilysin using a quenched fluorescent substance, on an isolated nerve cell (viable cell) or an immobilized nerve cell (preferably, an isolated and immobilized nerve cell).

The nerve cell used in the measuring method of the present invention is normally collected from any of brain regions (e.g., olfactory bulb, amygdaloid nucleus, basal ganglia, hippocampus, thalamus, hypothalamus, subthalamic nucleus, cerebral cortex, medulla oblongata, cerebellum, occipital lobes, frontal lobe, lateral lobe, putamen, caudate nucleus, corpus callosum, substantia nigra), using publicly known methods (methods described in, e.g., Culturing Nerve Cells (The MIT press, 1991), etc.). In one embodiment the cell is a human SH-SY5Y neuroblastoma cell.

A method of screening according to the present invention, a test compound is added to the cells and after incubation for a given period of time the cells are assayed for NEP activity using a substrate according to the present invention.

In the reactions described above, a quenched fluorogenic peptide used as the substrate is degraded by neprilysin or an amyloid β degrading enzyme. The quenched fluorogenic peptide comprises a fluorophore at one end (N- or C-terminal) and a quencher at the other end (C- or N-terminal, respectively) of the peptide which comprises an amino acid sequence sensitive to cleavage by an Aβ degrading enzyme activity. The cleavage releases the fluorophore from the attached quencher and Aβ degrading enzyme activity is monitored by detecting the amount of fluorescence released.

The enhanced neprilysin activity or gene expression can be quantified from the stained images obtained in the activity measurement described above by digitalizing its fluorescence intensity, using software for image analysis. As the software, there are used MetaVue from Nippon Roper Co., Ltd., and the like.

Drug Discovery

Compounds for enhancing the activity and/or expression of neprilysin can be efficiently screened using the neprilysin activity detection assay of the present invention. Such compounds include a compound having the effect of enhancing neprilysin activity, or a compound having the effect of increasing (or enhancing) the expression of neprilysin gene, and the like.

Compounds that enhance Neprilysin (NEP) activity are useful candidates for the degradation of Aβ as a therapy for Alzheimer's disease.

Compounds that inhibit Neprilysin (NEP) activity are useful inhibitors that can act as analgesic and antihypertensive agents by preventing neprilysin's activity against signaling peptides such as enkephalins, substance P, endothelin, and atrial natriuretic factor.

In cancer biomarker studies, the neprilysin gene is often referred to as CD10 or CALLA. In types of cancer where neprilysin is overexpressed, such as metastatic carcinoma and some advanced melanomas, compounds that inhibit Neprilysin (NEP) activity are useful agents. In other types of cancer, most notably lung cancers, where neprilysin is downregulated, compounds that enhance NEP activity are desired.

NEP enhancing compounds include, but are not limited to, peptides, such as angiotensin, bombesin, canavinoid, cholecystokinin, glutamine, serotonin, melatonin, neuropeptide Y, opioids, purines, vasopressin, oxytocin, substance P, PACAP, secretin, glucagon, calcitonin, adrenomedulin, somatostatin, GHRH, CRF, ACTH, GRP, PTH, VIP, dopamine, motilin, amylin, bradykinin, CGRP (calcitonin gene-related peptide), pancreastatin, thromboxane, adrenaline, the chemokine superfamily, endothelin, enterogastrin, histamine, neurotensin, TRH, pancreatic polypeptide, galanin, proteins, non-peptide compounds, synthetic compounds, fermentation products, cell extracts, vegetable extracts, animal tissue extracts, and small molecules. Preferred test compounds in the screening method of the present invention are a protein containing substantially the same amino acid sequence as somatostatin or its partial peptide, an agonist of somatostatin receptor or its salt, a protein containing substantially the same amino acid sequence as substance P or its partial peptide, an agonist of substance P receptor or its salt and, PACAP and VIP receptor antagonists.

In one embodiment, the screening assay revealed curcumin and curcumin analogs that either enhance or reduce NEP activity in a cell.

Compounds that inhibit IDE levels can be useful agents for the treatment of Alzheimer's disease by degrading amyloid-β or preventing oligomerization of Aβ or both.

The compounds tested as modulators of disaggregation activity or aggregation activity can be any small organic molecule, or a biological entity, such as a protein, e.g., an antibody or peptide, a sugar, a nucleic acid, e.g., an antisense oligonucleotide, RNAi, or a ribozyme, or a lipid. Alternatively, modulators can be genetically altered versions of a cellular modulator of disaggregation activity or aggregation activity. Typically, test compounds will be small organic molecules, peptides, lipids, and lipid analogs.

Essentially any chemical compound can be used as a potential modulator of NEP activity in the assays of the invention, although often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one embodiment, high throughput screening methods involve providing a combinatorial small organic molecule or peptide library containing a large number of potential therapeutic compounds (potential modulator or ligand compounds). Such “combinatorial chemical libraries” or “ligand libraries” are then screened in one or more assays, as described herein, to identify those library members (particular chemical species or subclasses) that display a desired characteristic activity. The compounds thus identified can serve as conventional “lead compounds” or can be used as potential or actual therapeutics.

A combinatorial chemical library is a collection of diverse chemical compounds generated by either chemical synthesis or biological synthesis, by combining a number of chemical “building blocks” such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37: 487-493, 1991 and Houghton et al., Nature 354: 84-88, 1991). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90: 6909-6913, 1993), vinylogous polypeptides (Hagihara et al., J. Amer. Chem. Soc. 114: 6568, 1992), nonpeptidal peptidomimetics with glucose scaffolding (Hirschmann et al., J. Amer. Chem. Soc. 114: 9217-9218, 1992), analogous organic syntheses of small compound libraries (Chen et al., J. Amer. Chem. Soc. 116: 2661, 1994), oligocarbamates (Cho et al., Science 261: 1303, 1993), and/or peptidyl phosphonates (Campbell et al., J. Org. Chem. 59: 658, 1994), nucleic acid libraries (see Ausubel, Berger and Sambrook, all supra), peptide nucleic acid libraries (see, e.g., U.S. Pat. No. 5,539,083), antibody libraries (see, e.g., Vaughn et al, Nature Biotechnology, 14: 309-314, 1996 and PCT/US96/10287), carbohydrate libraries (see, e.g., Liang et al., Science 274: 1520-1522, 1996 and U.S. Pat. No. 5,593,853), small organic molecule libraries (see, e.g., benzodiazepines, Baum C&EN, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, R U, 3D Pharmaceuticals, Exton, Pa., Martek Biosciences, Columbia, Md., etc.).

The test compounds can be obtained using any of the numerous approaches in combinatorial library methods known in the art, including, but not limited to, biological libraries; spatially addressable parallel solid phase or solution phase libraries; synthetic library methods requiring deconvolution; the “one-bead one-compound” library method; and synthetic library methods using affinity chromatography selection. The biological library approach can be used for, e.g., peptide libraries, while the other four approaches are applicable to peptide, non-peptide oligomer or small molecule libraries of compounds (Lam, Anticancer Drug Des. 12: 145, 1997). Examples of methods for the synthesis of molecular libraries can be found in the art, for example in: DeWitt et al., Proc. Natl. Acad. Sci. U.S.A. 90: 6909, 1993; Erb et al., Proc. Natl. Acad. Sci. USA 91: 11422, 1994; Zuckermann et al., J. Med. Chem. 37: 2678, 1994; Cho et al., Science 261: 1303, 1993; Carrell et al., Angew. Chem. Int. Ed. Engl. 33: 2059, 1994; Carell et al., Angew. Chem. Int. Ed. Engl. 33: 2061, 1994; and Gallop et al., J. Med. Chem. 37: 1233, 1994.

Libraries of compounds can be presented in solution (e.g., Houghten, Bio/Techniques 13: 412-421, 1992), or on beads (Lam, Nature 354: 82-84, 1991), chips (Fodor, Nature 364: 555-556, 1993), bacteria (U.S. Pat. No. 5,223,409), spores (U.S. Pat. Nos. 5,571,698, 5,403,484, and 5,223,409), plasmids (Cull et al., Proc. Natl. Acad. Sci. USA 89: 1865-1869, 1992) or on phage (Scott et al., Science 249: 386-390, 1990; Devlin, Science 249: 404-406, 1990; Cwirla et al., Proc. Natl. Acad. Sci. USA 87: 6378-6382, 1990; and Felici, J. Mol. Biol. 222: 301-310, 1991).

Curcumin and Curcumin Analogs Screened by the Assay Methods

Candidate compounds that are useful as part of a strategy to identify drugs for treating disorders involving Aβ degrading enzyme activity are compounds having the effect of enhancing the activity or expression of neprilysin. The compounds ameliorate proteotoxicity and neurodegeneration associated with Alzheimer’s disease and related diseases. The assays can be cell-based or cell-free.

Figure 10:
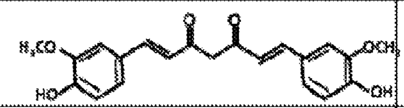
FIG. 10 shows the structures of screened compounds curcumin (compound 1) and curcumin analogs (compounds 2-26).
Figure 10:
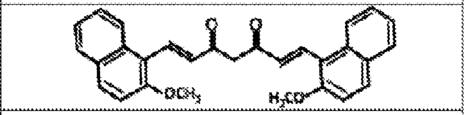
Figure 10:
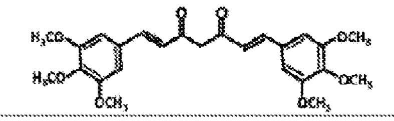
Figure 10:
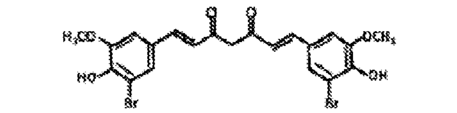
Figure 10:
Figure 10:
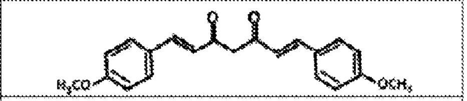
Figure 10:
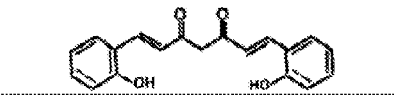
Figure 10:
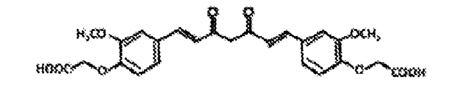
Figure 10:
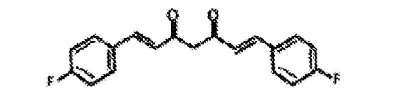
Figure 10:
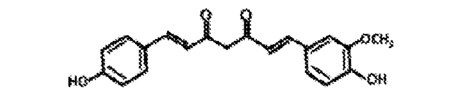
Figure 10:
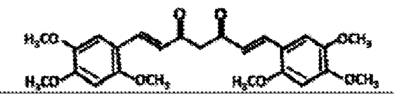
Figure 10:
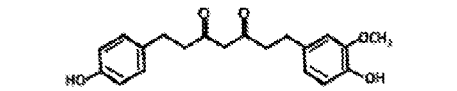
Figure 10:
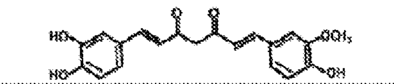
Figure 10:
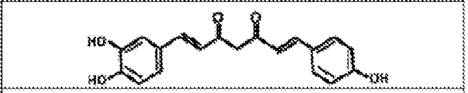
Figure 10:
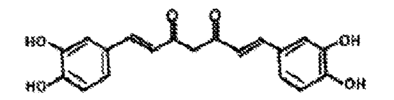
Figure 10:
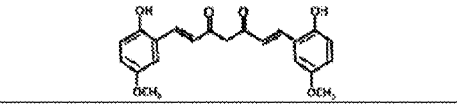
Figure 10:
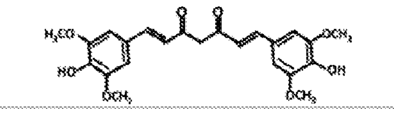
Figure 10:
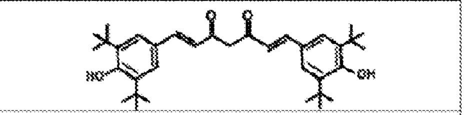
Figure 10:
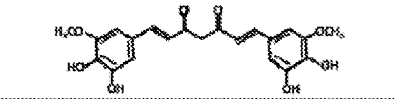
Figure 10:
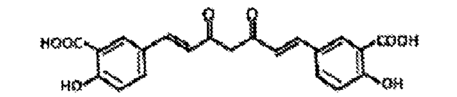
Figure 10:
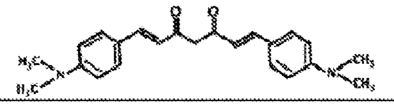
Figure 10:
Figure 10:
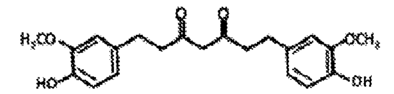
Figure 10:
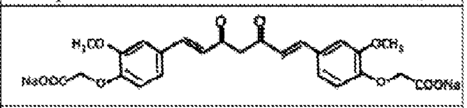
Figure 10:
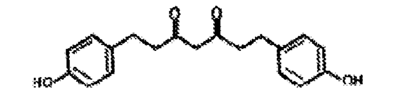
Figure 10:
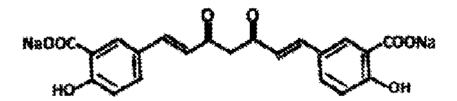

In one aspect of the invention, 26 compounds representing curcumin and curcumin analogs, as shown in Table 1 below, were screened using qf-Aβ(1-7)C as peptide substrate in the screening assay. The structures of curcumin (Compound 1) and curcumin analogs (Compounds 2-26) are as shown in FIG. 10.

TABLE 1

| | |
|---|---|
| Compound 1 | 1,7-Bis(4-hydroxy-3-methoxyphenyl)-1,6-heptadiene-3,5-dione |
| Compound 2 | 1,7-Bis(3,4,5-trimethoxyphenyl)-1,6-heptadiene-3,5-dione |
| Compound 3 | 1,7-Bis(4-hydroxyphenyl)-1,6-heptadiene-3,5-dione |
| Compound 4 | 1,7-Bis(2-hydroxyphenyl)-1,6-heptadiene-3,5-dione |
| Compound 5 | 1,7-Bis(4-fluorophenyl)-1,6-heptadiene-3,5-dione |
| Compound 6 | 1,7-Bis(2,4,5-trimethoxyphenyl)-1,6-heptadiene-3,5-dione |
| Compound 7 | 1-(3,4-Dihydroxyphenyl)-7-(3-methoxy-4-hydroxyphenyl)-1,6-heptadiene-3,5-dione |
| Compound 8 | 1,7-Bis(3,4-dihydroxyphenyl)-1,6-heptadiene-3,5-dione |
| Compound 9 | 1,7-Bis(4-hydroxy-3,5-dimethoxyphenyl)-1,6-heptadiene-3,5-dione |
| Compound 10 | 1,7-Bis(3,4-dihydroxy-5-methoxyphenyl)-1,6-heptadiene-3,5-dione |
| Compound 11 | 1,7-Bis(4-N,N-dimethylaminophenyl)-1,6-heptadiene-3,5-dione |
| Compound 12 | 1,7-Bis(4-hydroxy-3-methoxyphenyl)heptan-3,5-dione |
| Compound 13 | 1,7-Bis(4-hydroxyphenyl)heptan-3,5-dione |
| Compound 14 | 1,7-Bis(2-methoxy-1-naphthyl)-1,6-heptadiene-3,5-dione |
| Compound 15 | 1,7-Bis(3-bromo-4-hydroxy-5-methoxyphenyl)-1,6-heptadiene-3,5-dione |
| Compound 16 | 1,7-Bis(4-methoxyphenyl)-1,6-heptadiene-3,5-dione |
| Compound 17 | 1,7-Bis(3-methoxy-4-carboxymethoxyphenyl)-1,6-heptadiene-3,5-dione |
| Compound 18 | 1-(4-Hydroxyphenyl)-7-(4-hydroxy-3-methoxyphenyl)-1,6-heptadiene-3,5-dione |
| Compound 19 | 1-(4-Hydroxyphenyl)-7-(4-hydroxy-3-methoxyphenyl)-heptan-3,5-dione |
| Compound 20 | 1-(3,4-dihydroxyphenyl)-7-(4-hydroxyphenyl)-1,6-heptadiene-3,5-dione |
| Compound 21 | 1,7-Bis(2-hydroxy-5-methoxyphenyl)-1,6-heptadiene-3,5-dione |
| Compound 22 | 1,7-Bis(3,5-di-tert-butyl-4-hydroxyphenyl)-1,6-heptadiene-3,5-dione |
| Compound 23 | 1,7-Bis(3-carboxy-4-hydroxyphenyl)-1,6-heptadiene-3,5-dione |
| Compound 24 | 1,7-Bis(3,4-dimethoxyphenyl)-1,6-heptadiene-3,5-dione |
| Compound 25 | 1,7-Bis(3-methoxy-4-carboxymethoxyphenyl)-1,6-heptadiene-3,5-dione sodium salt |
| Compound 26 | 1,7-bis(3-carboxy-4-hydroxyphenyl)-1,6-heptadiene-3,5-dione disodium salt |

Figure 11:
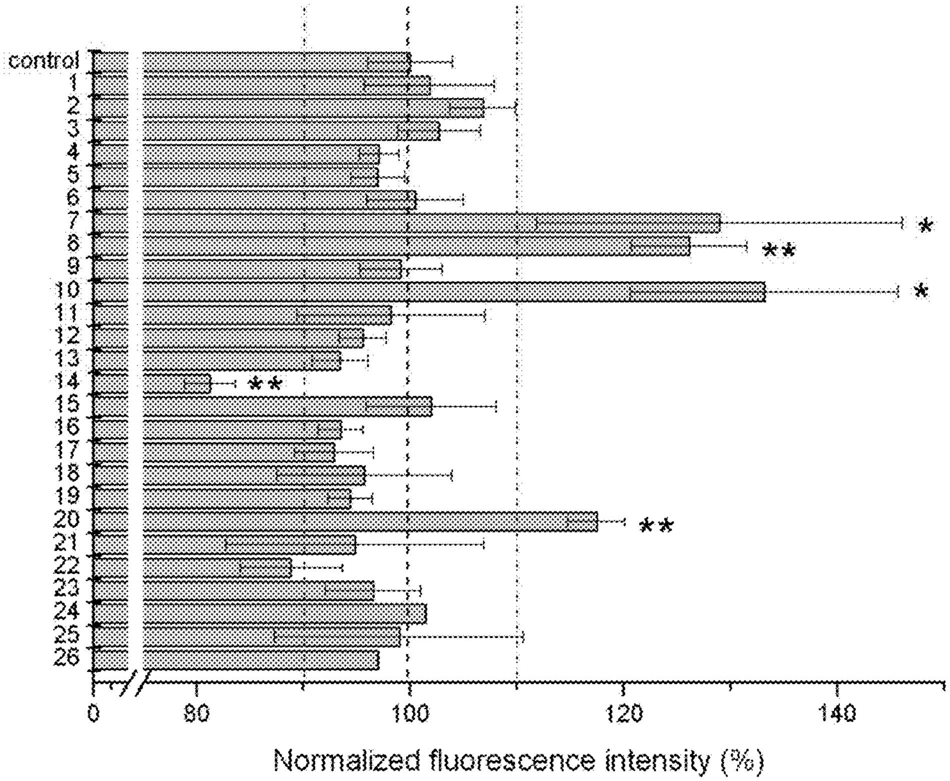
FIG. 11 shows the NEP activity of human SHSY5Y cells treated with curcumin and curcumin analogs using qf-Aβ(1-7)C as peptide substrate in the screening assay. The compound number is indicated on the left of each bar. Curcumin analogs 7, 8, 10 and 20 show large enhancements of NEP activity whereas curcumin analog 14 decreases NEP activity by nearly 20%. (**, p value<0.001; *, p value<0.01).

As shown in FIG. 11, the NEP activities of human SHSY5Y cells treated with curcumin and curcumin analogs (Compounds 1-26) were screened using qf-Aβ(1-7)C as peptide substrate in the screening assay. Analogs comprising at least three hydroxyl groups attached to the two aromatic rings of the curcumin structure scaffold (Compound 1) were particularly active in enhancing NEP activity. Curcumin analog compounds 7, 8, 10 and 20 largely enhanced NEP activity whereas analog compound 14 decreased NEP activity.

This invention further pertains to novel agents identified by the above-described screening assays and uses thereof for treatments as described herein. The compound obtained using the screening method is a compound selected from the test compounds identified by the assays of the invention and has the effect of enhancing the activity or expression of neprilysin. The compound can be used as a pharmaceutical, such as a safe and low toxic preventive and/or therapeutic agent for Alzheimer's disease, etc. In addition, compounds derived from the compound obtained by the screening described above can be used as well.

The invention further includes pharmaceutical formulations including a novel agent identified by methods of the present invention, and a pharmaceutically acceptable carrier, excipient, or stabilizer (Remingion's Pharmaceutical Sciences 16th edition, Osol, A. Ed. (1980)). In certain embodiments, pharmaceutical formulations are prepared to enhance the stability of the agent during storage, e.g., in the form of lyophilized formulations or aqueous solutions.

The pharmaceutical compositions of antibodies of the invention may be used to treat or prevent and/or retard the progression of Alzheimer's disease.

In prophylactic applications, pharmaceutical compositions are administered to a patient susceptible to, or otherwise at risk of Alzheimer's disease or condition in a prophylactically effective amount. At-risk individuals include, but are not limited to, individuals with a family history of Alzheimer's disease. Alternatively stated, an at-risk individual is any individual who is believed to be at a higher risk than the general population for developing Alzheimer's disease. The term "prophylactically effective amount" is meant to refer to an amount of a formulation which produces an effect observed as the prevention of the onset of Alzheimer's disease. Prophylactically effective amounts of a formulation are typically determined by the effect they have compared to the effect observed when a second formulation lacking the active agent is administered to a similarly situated individual.

In therapeutic applications, compositions are administered to a patient suspected of, or already suffering from Alzheimer's disease in a therapeutically effective amount sufficient to cure, or at least partially arrest, the symptoms of the disease (biochemical and/or histological), including its complications and intermediate pathological phenotypes in development of the disease.

In both prophylactic and therapeutic regimes, agents are usually administered in several dosages until a sufficient response has been achieved. Typically, the response is monitored and repeated dosages are given if the response starts to wane. Effective doses vary depending upon many different factors, including means of administration, target site, physiological state of the patient, whether the patient is human or an animal, other medications administered, and whether treatment is prophylactic or therapeutic. Usually, the patient is a human but nonhuman mammals can also be treated.

The invention provides pharmaceutical compositions comprising one or more agents for the treatment of Alzheimer's disease, formulated together with a pharmaceutically acceptable carrier. Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). In certain embodiments, the therapeutic formulation preferably comprises the polypeptide or antibody at a concentration of between 5-200 mg/ml, preferably between 10-100 mg/ml.

The formulations herein may also contain one or more additional therapeutic agents suitable for the treatment of the Alzheimer's disease, or to prevent undesired side-effects. Preferably, the additional therapeutic agent has an activity complementary to the agent of the resent invention, and the two do not adversely affect each other. Such molecules are suitably present in the pharmaceutical formulation in amounts that are effective for the purpose intended.

The active ingredients of the invention and other therapeutic agents, are also entrapped in microcapsules prepared, for example, by coacervation techniques or by interfacial polymerization, for example, hydroxymethylcellulose or gelatin-microcapsules and polymethylmethacylate) microcapsules, respectively, in colloidal drug delivery systems (for example, liposomes, albumin microspheres, microemulsions, nanoparticles and nanocapsules) or in macroemulsions. Such techniques are disclosed in Remingion's Pharmaceutical Sciences 16th edition, Osol, A. Ed. (1980).

Sustained-release preparations may also be prepared. Suitable examples of sustained-release preparations include, but are not limited to, semi-permeable matrices of solid hydrophobic polymers containing the antibody, which matrices are in the form of shaped articles, e.g., films, or microcapsules. Non-limiting examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxy buryric acid.

Formulations to be used for in vivo administration are preferably sterile. This is readily accomplished by filtration through sterile filtration membranes The neprilysin activity measured by a method of the present invention, further allows presymptomatic diagnosis, stratification or diagnosis of Alzheimer's disease. Results obtained by the activity measurement of the present invention are quantified and the quantified values are compared with those obtained with a control (non-AD) sample. It enables prediction of a risk of developing Alzheimer's disease in a subject exhibiting dementia or pre-dementia.

Any one of the assays described herein can be adapted for high throughput screening. In the high throughput assays of the invention, either soluble or solid state, it is possible to screen up to several thousand different modulators or ligands in a single day. Only 200 μl culture medium is enough for detection of a substrate according to the present invention. One milligram of the synthetic peptide substrate can be used to screen more than six thousand compounds. It is ideal for high throughput screening compounds which can enhance neprilysin production of cell. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

EXAMPLES

Without further elaboration, it is believed that one skilled in the art can, using the preceding description, utilize the present invention to its fullest extent. The following examples are illustrative only, and not limiting of the remainder of the disclosure in any way whatsoever.

Example 1

Synthesis of the Peptide Substrate Aβ(1-7)C for Detecting amyloid-β-Degrading Enzymes The peptide Aβ(1-7)C (sequence DAEFRHDC), corresponding to residues 1 to 7 of the Aβ peptide followed by a cysteine residue, was prepared by the Fmoc-polyamide method on a PS3 peptide synthesizer (Rainin, USA). Preloaded Fmoc-Cys-Wang resin (substitution 0.58 mmol/g) was purchased from Anaspec Inc. (USA) and used in the synthesis. Fmoc-amino acid derivatives (0.4 mmol) were coupled to 0.1 mmol of resin using 0.4 mmol of benzotriazole-1-yl-oxy-tris-pyrrolidino-phosphonium hexafluorophosphate in dimethylformamide (DMF) containing 4.45% (v/v) of N-methyl morpholine. Fmoc cleavage was performed using 20% (v/v) piperidine in DMF. The peptides were cleaved from the resin by stirring at room temperature for 1-2 h with a mixture of 9.4 mL of trifluoroacetic acid, 0.1 mL of triisopropylsilane, 0.25 mL of water, and 0.25 mL of ethanedithiol and precipitated with three volumes of ice-cold methyl t-butyl ether by centrifugation at 2000 g for 10 minutes at 4° C., then the pellet was washed a further two times with methyl t-butyl ether and dried under vacuum. The resulting white powder was purified by reverse-phase HPLC using a Vydac C18 column (10 mm×250 mm) and acetonitrile-water mixtures containing 0.1% (v/v) trifluoroacetic acid. The final product was analyzed on a matrix-assisted laser desorption ionization (MALDI) mass spectrometer. Fractions containing the desired product were lyophilized and stored at −20° C.

Example 2

Synthesis of the Quenched Fluorogenic Peptide Substrate

The thiol-reactive Alexa-350 (Alexa Fluor® 350 $C_5$-maleimide) and amine-reactive Dabcyl (4-(4'-N,N-dimethylaminophenyl)azobenzoic acid) (Invitrogen) were used as the fluorescence donor and quencher, respectively. The cysteine residue at the C-terminus of Aβ(1-7)C was used to attach the thiol-reactive donor. Alexa-350 is optimally excited at 346 nm and has bright blue fluorescence emission. Dabcyl was added to the N-terminus of the peptide. Peptide Aβ(1-7)C was dissolved in a mixture of 10 mM Tris-HCl/DMSO [1/2.3 (v/v), pH 7.2] at a final concentration of 1.6 mM. One milliliter of peptide solution was taken and 17.3 μL of 50 mM TCEP (tris(2-carboxyethyl)phosphine) added to avoid disulfide bond formation, then 43 μL of 40 mM Alexa-350 in DMSO was added dropwise and the mixture reacted overnight with gentle inversion at room temperature. The Alexa-350-labeled peptide was separated from the unlabeled peptide free Alexa-350 by reverse-phase HPLC (FIG. 1A). The purified Alexa-350-labeled Aβ(1-7)C had an emission maximum at about 440 nm when excited at 346 nm. To add the quenching group, the Alexa-350-labeled peptide was dissolved in DMSO at a concentration of 1 mM and a 10-fold molar excess of Dabcyl powder was added. Fifty microliters of 100 mM sodium bicarbonate was added to 950 μL of the reaction mixture and the mixture incubated with gentle inversion for 2 h at room temperature. The double-labeled peptide qf-Aβ(1-7)C was purified by HPLC (FIG. 1B) and identified on a MALDI mass spectrometer as above. A peptide stock solution was prepared by dissolving the double-labeled peptide in DMSO to a final concentration of 1 mM and stored at −20° C.

Example 3

Fluorescence Spectroscopy 1.84 μM qf-Aβ(1-7)C in 50 mM Tris-HCl (pH 7.5) was reacted with 2 or 20 nM NEP at room temperature for 1 h in a 3-mm path-length rectangular cuvette on a FP-750 spectrofluorometer (Jasco, Japan) and the fluorescence emission between 375 and 600 nm measured with excitation at 346 nm (FIG. 2).

Example 4

Fluorogenic Enzyme Assay

To determine the optimal substrate concentration in the fluorogenic enzyme assay, NEP (0.5 mg/mL) and substrate peptide qf-Aβ(1-7)C (1 mM) were mixed in 50 mM Tris-HCl (pH 7.5), 25 mM NaCl, 5 μM $ZnCl_2$ to a final NEP concentration of 0.92 nM and peptide concentrations of 0.46, 0.92, 1.84, 3.68, or 7.36 μM and placed on a 96-well plate (Corning, USA). The final volume of the reaction solution was kept as 200 μL. The enzyme reaction was performed in the dark at 37° C. and the fluorescence was measured at 1, 2, 3, and 4 h with excitation at 360 nm and emission at 465 nm on a Paradigm™ Detection Platform (Beckman Coulter, USA) (FIG. 3). To determine the sensitivity of the assay for NEP, the final qf-Aβ (1-7)C concentration was increased to 1.84 μM and NEP concentration was varied as 0, 0.10, 0.46, 0.92, 1.84, 3.68, or 7.36 nM. The enzyme reaction was performed in the dark at 37° C. and the fluorescence was measured at 1, 2, 3, and 4 h. The data are shown as the average for three independent samples (FIG. 4).

Figure 6:
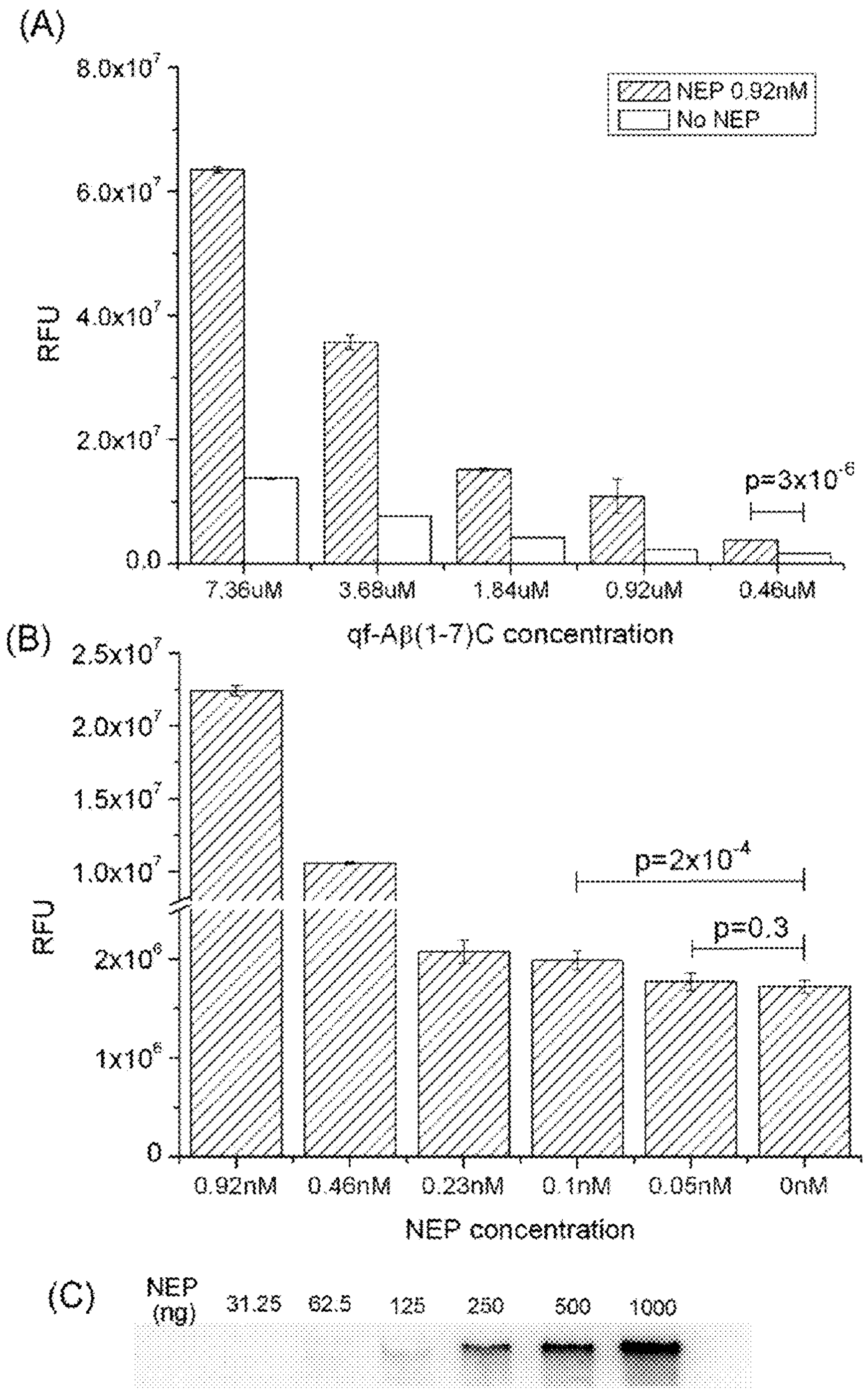
FIG. 6.

To determine the optimal reaction conditions, 0.92 nM NEP was reacted with different concentrations of qf-Aβ(1-7)C for 1 h at 37° C. (FIG. 6A). The result showed that 0.92 nM NEP could be detected when the substrate concentration was as low as 0.46 μM ($p=3\times10^{-6}$). To test whether the sensitivity of NEP detection was increased when a higher substrate concentration was used, the concentration of qf-Aβ (1-7)C was increased four times to 1.84 μM and reacted with different concentrations of NEP at 37° C. for 1 h (FIG. 6B). The result showed that NEP can be detected at concentrations as low as 0.1 nM (about 1.6 ng, $p=2\times10^{-4}$). The substrate concentration of 1.84 μM or higher was therefore used in the following studies. As depicted in FIG. 6C, anti-NEP antibody was observed to detect no lower than 125 ng of NEP, suggesting that the fluorogenic enzyme assay is 78 times more sensitive than the antibody detection method.

Example 5

Sensitivity of the Detection System for Different Aβ-Degrading Enzymes

Recombinant human NEP (0.5 mg/mL), insulin-degrading enzyme (IDE) (0.386 mg/mL), endothelin-converting enzyme 1 (ECE-1) (0.298 mg/mL), matrix metalloproteinases (MMP)-3 (0.124 mg/mL) and MMP-9 (0.5 mg/mL), and angiotensin-converting enzyme (ACE) (0.434 mg/mL) were purchased from R&D Systems (USA). Human plasmin (1 mM) was purchased from Sigma (USA). The enzymes were diluted in the following buffers as suggested by the manufacturer: 50 mM Tris-HCl (pH 7.5), 25 mM NaCl, 5 μM $ZnCl_2$ for NEP, IDE, ECE-1, and ACE; 50 mM Tris-HCl (pH 7.5), 150 mM NaCl, 10 mM $CaCl_2$, 0.05% Brij-35 for MMP-3 and MMP-9; and 50 mM Tris-HCl (pH 7.5) for plasmin. MMP-3 and MMP-9 were pre-activated by incubation at 37° C. for 24 h with 1 mM p-aminophenylmercuric acetate. The quenched fluorogenic peptide substrate qf-Aβ(1-7)C (0.4 μL of the 1 mM stock in DMSO) was mixed with different concentrations of enzyme solution (final peptide concentration 2 μM) on a 96-well plate. The final volume of the reaction solution was kept as 200 μL. The mixture was incubated in the dark for 1, 2, 3, or 4 h at 37° C., and then the fluorescence was measured with excitation at 360 nm and emission at 465 nm on a Paradigm™ Detection Platform (Beckman Coulter, USA) (FIG. 5).

The cleavage sites of various Aβ-degrading enzymes, NEP, IDE, ECE-1, ACE, various MMP, and plasmin on the Aβ peptide have been reported (Refs. 14, 15, 16). Among these, NEP, ACE, MMP-3, and plasmin were reported to cleave the N-terminal segment (sequence 1-7) of Aβ. When the ability of these enzymes to cleave the quenched fluorogenic peptide was compared, the results showed that only IDE and NEP were effective (FIG. 5). Surprisingly, the assay was even more sensitive to IDE than to NEP, despite the fact that no cleavage site for IDE in this peptide sequence has ever been previously reported. On the other hand, although it has been reported that MMP-3, plasmin, and ACE have a cleavage site within the sequence 1-7 of Aβ40 (14), no significant fluorescence increase was detected after 1-h digestion. ECE-1 and MMP-9 are also insensitive to this assay.

Figure 7:
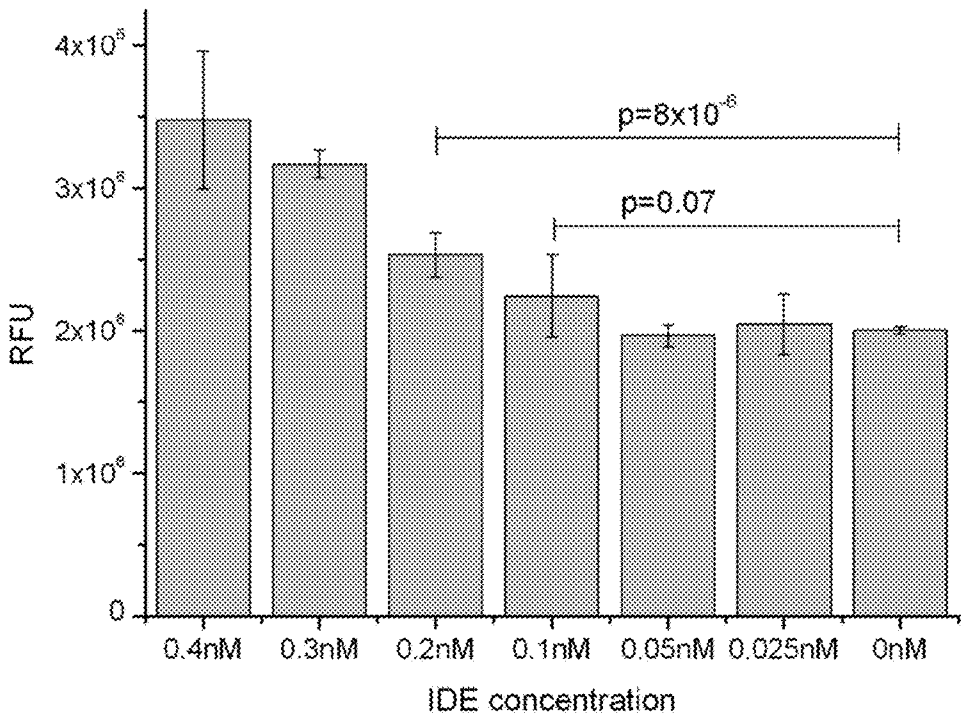
FIG. 7 shows fluorescence increase of 1.84 μM qf-Aβ(1-7)C after digestion with different concentrations of IDE at 37° C. for 1 hour.

The assay system was sensitive enough to detect as low as 0.10 nM NEP. Only 0.46 μM peptide substrate was sufficient for detecting 1 nM NEP, and only 2 μM peptide substrate was sufficient for detecting 0.1 nM NEP as compared to other known commercial substrates which require 40 μM peptide for detecting 2 nM NEP. To test the detection limit of the peptide substrate to IDE, qf-Aβ(1-7)C was reacted with different concentrations of IDE at 37° C. for 1 h (FIG. 7). It was found that as low as 0.2 nM IDE (about 4.6 ng) could be detected ($p=8\times10^{-6}$).

Example 6

Comparison with Commercially Available Quenched Fluorogenic Peptide

Figure 8:
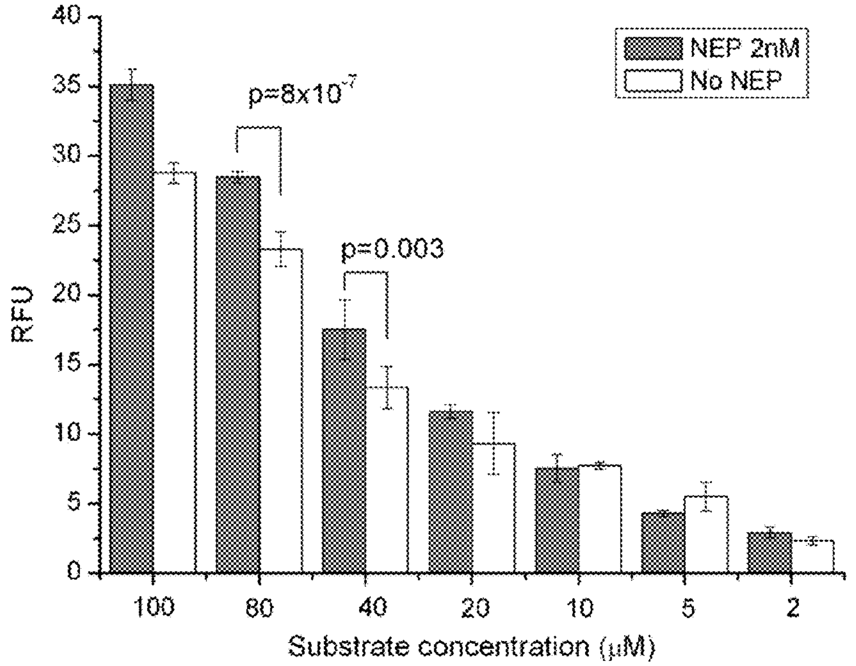
FIG. 8.
Figure 8:
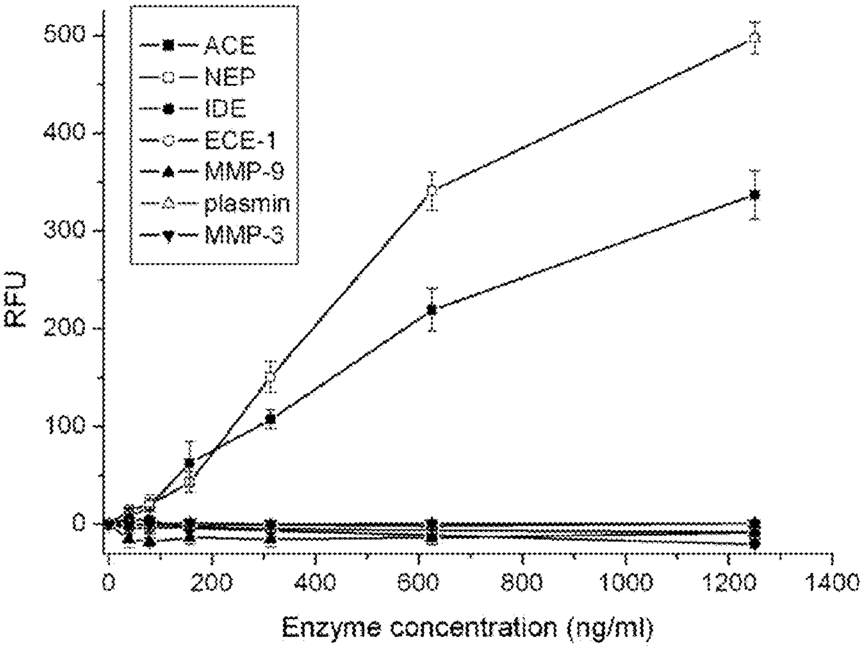

One commercially available quenched fluorogenic peptide substrate, Dansyl-$^{D}$AGF($pNO_2$)G, was tested for comparison. The fluorescence of dansyl is quenched by the presence of nitrophenyl group. Digestion was monitored by the fluorescence increase of dansyl at 562 nm when excited at 342 nm. The signal increase of Dansyl-$^{D}$AGF($pNO_2$)G after digestion is not strong enough, hence much higher peptide concentration (80 μM) is required for detecting 2 nMNEP (FIG. 8A) while only 0.46 μM of the peptide substrate are enough for detecting 0.92 nM NEP (FIG. 6A). This substrate also has enzyme specificity. It is sensitive to NEP and ACE (FIG. 8B). Because it is not sensitive to IDE, this substrate can be used to confirm whether the signal increase obtained in the qf-Aβ(1-7)C assay system is due to the activity of NEP or IDE.

Example 7

Detection of Somatostatin-Induced Aβ-Degrading Enzymes

Somatostatin is known to induce NEP production (30). Since NEP is a cell surface membrane-bound glycoprotein, the assay was performed in cell culture. AfterHuman SH-SY5Y cells (ATCC) were cultured in a 1:1 mixture of Dulbecco's modified Eagle's medium (Gibco, USA) supplemented with 10% fetal bovine serum (FBS; Biological industries, USA) in 5% $CO_2$ at 37° C. The cells were harvested, suspended at a density of about 830,000 cells/mL in the above medium without FBS and 600 μL plated in each well of a 12-well plate (TPP, Switzerland). Somatostatin purchased from Sigma was added to the cultures at a final concentration of 1 μM. The cells were incubated as above for 24 h, then qf-Aβ(1-7)C was added to each well at a final concentration of 2 μM and incubation continued. At 0, 1, 2, and 3 h, 100 μL of medium was taken for fluorescence measurement on a Varioskan® Flash 3001 (Thermo Electron Corporation, Finland) with excitation at 346 nm and emission at 436 nm. The average of three replicate wells was used for each sample and control, and the experiment was repeated at least three times (FIG. 9).

Without somatostatin treatment, there was a basal level of NEP production on the cell surface. After induction by somatostatin for one day, the fluorescence intensity after 1 h of digestion was ~58% higher.

Example 8

Method for Screening Compounds

Human SH-SY5Y cells were cultured in the Dulbecco's modified Eagle's medium (DMEM, Gibco, USA) supplemented with 10% fetal bovine serum (FBS; Biological industries, USA) in 5% $CO_2$ at 37° C. The cells were harvested and re-suspended in the phenol red-free DMEM medium supplemented with 10% FBS at a density of $1\times10^6$ cells/mL. 100 μL of cell culture was added in each well of a 96-well plate. The compounds (no. 1 to no. 24) were dissolved in DMSO, and the others (no. 25 and no. 26) were dissolved in sterilized water to make the stock solution (1 mM). Each compound was mixed with phenol red-free DMEM supplemented with 10% FBS to a final concentration of 10 μM. 100 μL of the medium containing 10 μM indicated compound was added into the wells to make the final compound concentration 5 μM. After incubation for 24 hr, the medium of the culture was replaced with the phenol red-free DMEM medium (not FBS) containing 2 μM qf-Aβ(1-7)C and incubation continued for additional 1 h. To measure the proteolytic activity, 100 μL of the medium was taken out for fluorescence measurement on SpectraMax Gemini EM (Molecular Devices, USA) with excitation at 346 nm and emission at 442 nm. The average of three replicate wells was used for each sample and control.

REFERENCES

[1] R. Brookmeyer, S. Gray, and C. Kawas, Projections of Alzheimer's disease in the United States and the public health impact of delaying disease onset. Am. J. Public Health 88 (1998) 1337-1342.

[2] D. J. Selkoe, The molecular pathology of Alzheimer's disease. Neuron 6 (1991) 487-498.

[3] G. G. Glenner, and C. W. Wong, Alzheimers-disease and Downs-syndrome—sharing of a unique cerebrovascular amyloid fibril protein. Biochem. Biophys. Res. Commun. 122 (1984) 1131-1135.

[4] C. L. Masters, G. Simms, N. A. Weinman, G. Multhaup, B. L. Mcdonald, and K. Beyreuther, Amyloid plaque core protein in Alzheimer-disease and Down syndrome. Proc. Nat. Acad. Sci. USA 82 (1985) 4245-4249.

[5] S. Gandy, The role of cerebral amyloid b accumulation in common forms of Alzheimer disease. J. Clin. Invest. 115 (2005) 1121-1129.

[6] J. A. Hardy, and G. A. Higgins, Alzheimers-disease—the amyloid cascade hypothesis. Science 256 (1992) 184-185.

[7] J. Hardy, and D. J. Selkoe, The amyloid hypothesis of Alzheimer's disease: progress and problems on the road to therapeutics. Science 297 (2002) 353-356.

[8] W. Farris, S. G. Schutz, J. R. Cirrito, G. M. Shankar, X. Sun, A. George, M. A. Leissring, D. M. Walsh, W. Q. Qiu, D. M. Holtzman, and D. J. Selkoe, Loss of neprilysin function promotes amyloid plaque formation and causes cerebral amyloid angiopathy. Am. J. Pathol. 171 (2007) 241-251.

[9] M. S. Rafii, and P. S. Aisen, Recent developments in Alzheimer's disease therapeutics. BMC Med 7 (2009) 7.

[10] R. Jakob-Roetne, and H. Jacobsen, Alzheimer's disease: from pathology to therapeutic approaches. Angew. Chem. Int. Ed. 48 (2009) 3030-3059.

[11] E. R. L. C. Vardy, A. J. Catto, and N. M. Hooper, Proteolytic mechanisms in amyloid-b metabolism: therapeutic implications for Alzheimer's disease. Trends Mol. Med. 11 (2005) 464-472.

[12] S. Chen, X. J. Zhang, L. Li, and W. D. Le, Current experimental therapy for Alzheimer's disease. Curr. Neuropharmacol. 5 (2007) 127-134.

[13] Y. J. Wang, H. D. Zhou, and X. F. Zhou, Clearance of amyloid-b in Alzheimer's disease: progress, problems and perspectives. Drug Discov. Today 11 (2006) 931-938.

[14] A. J. Turner, and N. N. Nalivaeva, New insights into the roles of metalloproteinases in neurodegeneration and neuroprotection. Int. Rev. Neurobiol. 82 (2007) 113-135.

[15] E. A. Eckman, and C. B. Eckman, Ab-degrading enzymes: modulators of Alzheimer's disease pathogenesis and targets for therapeutic intervention. Biochem. Soc. Trans. 33 (2005) 1101-1105.

[16] N. N. Nalivaeva, L. R. Fisk, N. D. Belyaev, and A. J. Turner, Amyloid-degrading enzymes as therapeutic targets in Alzheimer's disease. Curr. Alzheimer Res. 5 (2008) 212-224.

[17] S. S. El-Amouri, H. Zhu, J. Yu, R. Marr, I. M. Verma, and M. S. Kindy, Neprilysin: an enzyme candidate to slow the progression of Alzheimer's disease. Am. J. Pathol. 172 (2008) 1342-1354.

[18] L. B. Hersh, and D. W. Rodgers, Neprilysin and amyloid b Peptide degradation. Curr. Alzheimer Res. 5 (2008) 225-231.

[19] Y. Ling, K. Morgan, and N. Kalsheker, Amyloid precursor protein (APP) and the biology of proteolytic processing: relevance to Alzheimer's disease. Int. J. Biochem. Cell Biol. 35 (2003) 1505-1535.

[20] J. A. Carson, and A. J. Turner, b-Amyloid catabolism: roles for neprilysin (NEP) and other metallopeptidases? J. Neurochem. 81 (2002) 1-8.

[21] R. A. Marr, H. Guan, E. Rockenstein, M. Kindy, F. H. Gage, I. Verma, E. Masliah, and L. B. Hersh, Neprilysin regulates amyloid b peptide levels. J. Mol. Neurosci. 22 (2004) 5-11.

[22] A. Caccamo, S. Oddo, M. C. Sugarman, Y. Akbari, and F. A. LaFerla, Age- and region-dependent alterations in Ab-degrading enzymes: implications for Ab-induced disorders. Neurobiol. Aging 26 (2005) 645-654.

[23] D. S. Wang, N. Iwata, E. Hama, T. C. Saido, and D. W. Dickson, Oxidized neprilysin in aging and Alzheimer's disease brains. Biochem. Biophys. Res. Commun. 310 (2003) 236-241.

[24] M. Carpentier, Y. Robitaille, L. DesGroseillers, G. Boileau, and M. Marcinkiewicz, Declining expression of neprilysin in Alzheimer disease vasculature: possible involvement in cerebral amyloid angiopathy. J. Neuropathol. Exp. Neurol. 61 (2002) 849-856.

[25] H. Kanemitsu, T. Tomiyama, and H. Mori, Human neprilysin is capable of degrading amyloid b peptide not only in the monomeric form but also the pathological oligomeric form. Neurosci. Lett. 350 (2003) 113-116.

[26] N. Iwata, S. Tsubuki, Y. Takaki, K. Shirotani, B. Lu, N. P. Gerard, C. Gerard, E. Hama, H. J. Lee, and T. C. Saido, Metabolic regulation of brain Ab by neprilysin. Science 292 (2001) 1550-1552.

[27] K. Barnes, A. J. Turner, and A. J. Kenny, Membrane localization of endopeptidase-24.11 and peptidyl dipeptidase A (angiotensin converting enzyme) in the pig brain: a study using subcellular fractionation and electron microscopic immunocytochemistry. J. Neurochem. 58 (1992) 2088-2096.

[28] N. Iwata, M. Higuchi, and T. C. Saido, Metabolism of amyloid-b peptide and Alzheimer's disease. Pharmacol. Therapeut. 108 (2005) 129-148.

[29] A. Chersi, S. Ferracuti, G. Falasca, R. H. Butler, and D. Fruci, Assembly and selective "in synthesis" labeling of quenched fluorogenic protease substrates. Anal. Biochem. 357 (2006) 194-199.

[30] T. Saito, N. Iwata, S. Tsubuki, Y. Takaki, J. Takano, S. M. Huang, T. Suemoto, M. Higuchi, and T. C. Saido, Somatostatin regulates brain amyloid b peptide Ab42 through modulation of proteolytic degradation. Nat. Med. 11 (2005) 434-439.

[31] G. Evin, and A. Weidemann, Biogenesis and metabolism of Alzheimer's disease Ab amyloid peptides. Peptides 23 (2002) 1285-1297.

[32] K. M. Carvalho, G. Boileau, A. C. M. Camargo, and L. Juliano, A highly selective assay for neutral endopeptidase based on the cleavage of a fluorogenic substrate related to Leu-Enkephalin. Anal. Biochem. 237 (1996) 167-173.

[33]C. Llorens, B. Malfroy, J. C. Schwartz, G. Gacel, B. P. Rogues, J. Roy, J. L. Morgat, F. Javoy-Agid, and Y. Agid, Enkephalin dipeptidyl carboxypeptidase (enkephalinase) activity: selective radioassay, properties, and regional distribution in human brain. J. Neurochem. 39 (1982) 1081-1089.

[34]J. S. Miners, P. G. Kehoe, and S. Love, Immunocapture-based fluorometric assay for the measurement of insulin-degrading enzyme activity in brain tissue homogenates. J. Neurosci. Methods 169 (2008) 177-181.

[35]J. S. Miners, M. M. Verbeek, M. O. Rikkert, P. G. Kehoe, and S. Love, Immunocapture-based fluorometric assay for the measurement of neprilysin-specific enzyme activity in brain tissue homogenates and cerebrospinal fluid. J. Neurosci. Methods 167 (2008) 229-236.

[36] W. C. Duckworth, R. G. Bennett, and F. G. Hamel, Insulin degradation: progress and potential. Endocr. Rev. 19 (1998) 608-624.

[37] Chagas J R, Juliano L, Prado E S. Intramolecularly quenched fluorogenic tetrapeptide substrates for tissue and plasma kallikreins. *Anal. Biochem.*, 1991; 192: 419-25.

[38] Velasquez, Elsa F.; Molly Yancovitz, Anna Pavlick, Russell Berman, Richard Shapiro, Dusan Bogunovic, David O'Neill, Yi-Lo Yu, Joanna Spira, Paul J Christos, Xi Kathy Zhou, Madhu Mazumdar, David M Nanus, Leonard Liebes, Nina Bhardwaj, David Polsky and Iman Osman (January 2007). Clinical relevance of Neutral Endopeptidase (NEP/CD10) in melanoma. Journal of Translational Medicine 5 (2): 2.

[39] Oefner, C.; B. P. Rogues, M.-C. Fournie-Zaluski and G. E. Dale (February 2004). Structural analysis of neprilysin with various specific and potent inhibitors. *Acta Crystallographica D* 60 (Pt 2): 392-396.

[40] Kurochkin I V, Goto S (1994). "Alzheimer's beta-amyloid peptide specifically interacts with and is degraded by insulin degrading enzyme". *FEBS Lett.* 345 (1): 33-7.

[41] Wei Qiao Qiu, Dominic M. Walsh, Zhen Ye, Konstantinos Vekrellis, Jimin Zhang, Marcia B. Podlisny, Marsha Rich Rosner‡, Afshin Safavi§, Louis B. Hersh§ and Dennis J. Selkoe (1998). "Insulin-degrading Enzyme Regulates Extracellular Levels of Amyloid β-Protein by Degradation". *The Journal of Biological Chemistry* 273 (49): 32730-8.

All publications and patent applications cited in this specification are herein incorporated by reference as if each individual publication or patent application was specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of enhancing neprilysin activity and/or degrading amyloid-β peptides and/or oligomers in a subject with Alzheimer's disease, comprising:

administering to the subject a compound selected from the group consisting of

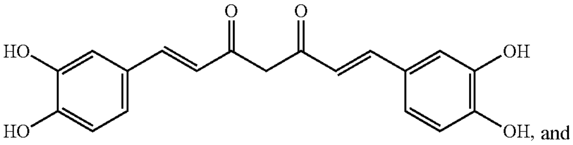

and

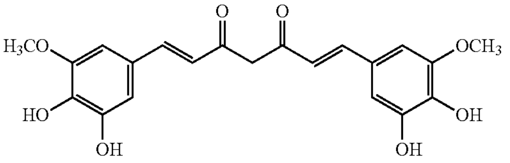

in a therapeutically effective amount to enhance the neprilysin activity and/or degrade the amyloid-β peptides and oligomers in the subject.

2. A method of improving symptoms and/or retarding progression of Alzheimer's disease, comprising:

administering to a subject with the Alzheimer's disease a Compound selected from the group consisting of

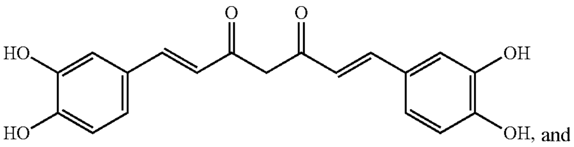

and

-continued

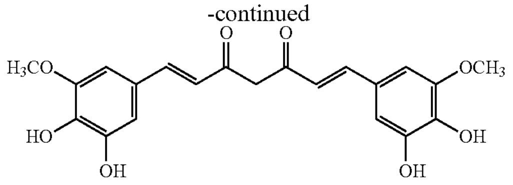

in a therapeutically effective amount to improve symptoms and/or retard progression of the Alzheimer's disease in the subject.

3. A method for prophylactic treatment and/or treatment of Alzheimer's disease, comprising:

administering to a subject in need thereof a compound selected from the group consisting of

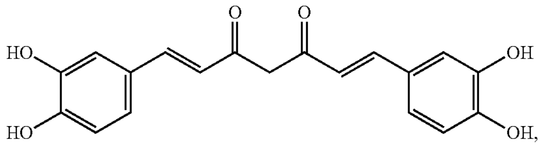

, and

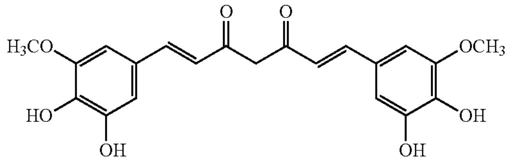

in a therapeutically effective amount to prophylactically treat and/or treat the Alzheimer's disease in the subject.

* * * * *

UNITED STATES PATENT AND TRADEMARK OFFICE

CERTIFICATE OF CORRECTION

PATENT NO. : 9,074,238 B2
APPLICATION NO. : 13/467036
DATED : July 7, 2015
INVENTOR(S) : Rita P.-Y. Chen et al.

It is certified that error appears in the above-identified patent and that said Letters Patent is hereby corrected as shown below:

On the Title Page, Item (12), delete “Hu et al.” and substitute --Chen et al.--

On the Title Page, Item (75), delete “Chaur-Jong Hu, Taipei (TW); Po-Ting Chen, Taipei (TW); Rita P.-Y. Chen, Taipei (TW); Steven Sheng-Shih Wang, Taipei (TW)”

and substitute --Rita P.-Y. Chen, Taipei (TW); Steven Sheng-Shih Wang, Taipei (TW); Chaur-Jong HU, Taipei (TW); Po-Ting Chen, Taipei (TW)--

Signed and Sealed this
Thirteenth Day of October, 2015

Michelle K. Lee
*Director of the United States Patent and Trademark Office*